United States Patent [19]

Robinson et al.

[11] Patent Number: 5,973,141
[45] Date of Patent: Oct. 26, 1999

[54] METHOD FOR THE DEMETHOXYCARBONYLATION OF PORPHYRINIC COMPOUNDS SUCH AS PHEOPHORBIDES

[75] Inventors: Byron C. Robinson, Santa Barbara; Avinash S. Phadke, Goleta; Shwn-Ji Susie Hwang Lee, Goleta; Dipanjan Sengupta, Goleta, all of Calif.

[73] Assignee: Miravant Pharmaceuticals, Inc., Santa Barbara, Calif.

[21] Appl. No.: 09/188,017

[22] Filed: Nov. 27, 1998

[51] Int. Cl.[6] ................................................ C07D 487/22
[52] U.S. Cl. ............................................ 540/145; 534/15
[58] Field of Search ............................ 540/145; 8534/15

[56] References Cited

U.S. PATENT DOCUMENTS 5,198,460   3/1993   Pandey et al. ........................ 514/410
5,506,255   4/1996   Smith et al. ......................... 514/410

*Primary Examiner*—Richard L. Raymond
*Assistant Examiner*—Pavanaram K Sripada
*Attorney, Agent, or Firm*—Finnegan, Henderson, Farabow, Garrett & Dunner, L.L.P.

[57] ABSTRACT

An improved method for the demethoxycarbonylation of porphyrinic compounds such as pheophorbides involving reacting the starting porphyrinic compound with a high boiling point solvent to which a selected amount of water has been added.

46 Claims, 35 Drawing Sheets

Figure 1. Demethoxycarbonylation of methyl pheophorbide (100 mg) in distilled collidine*/water (2 equiv.)
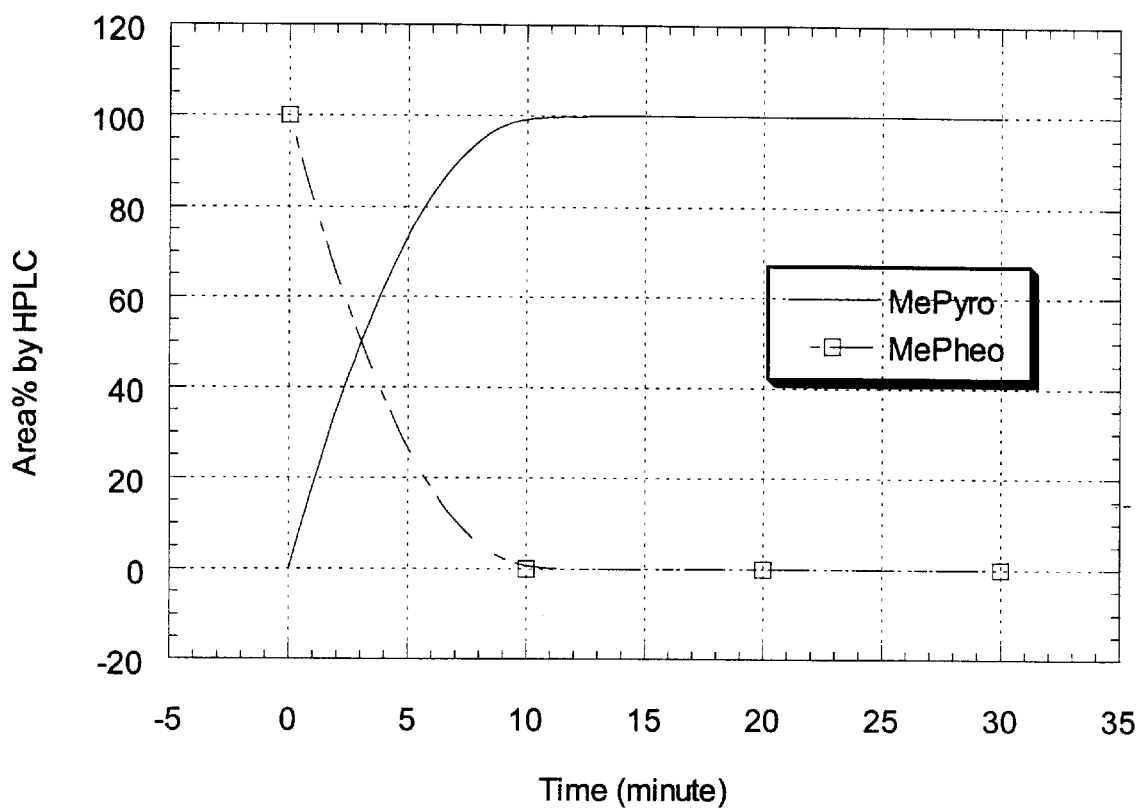
* Collidine was distilled and stored over molecular sieves (4A) in a round bottom flask sealed by a glass stopper.

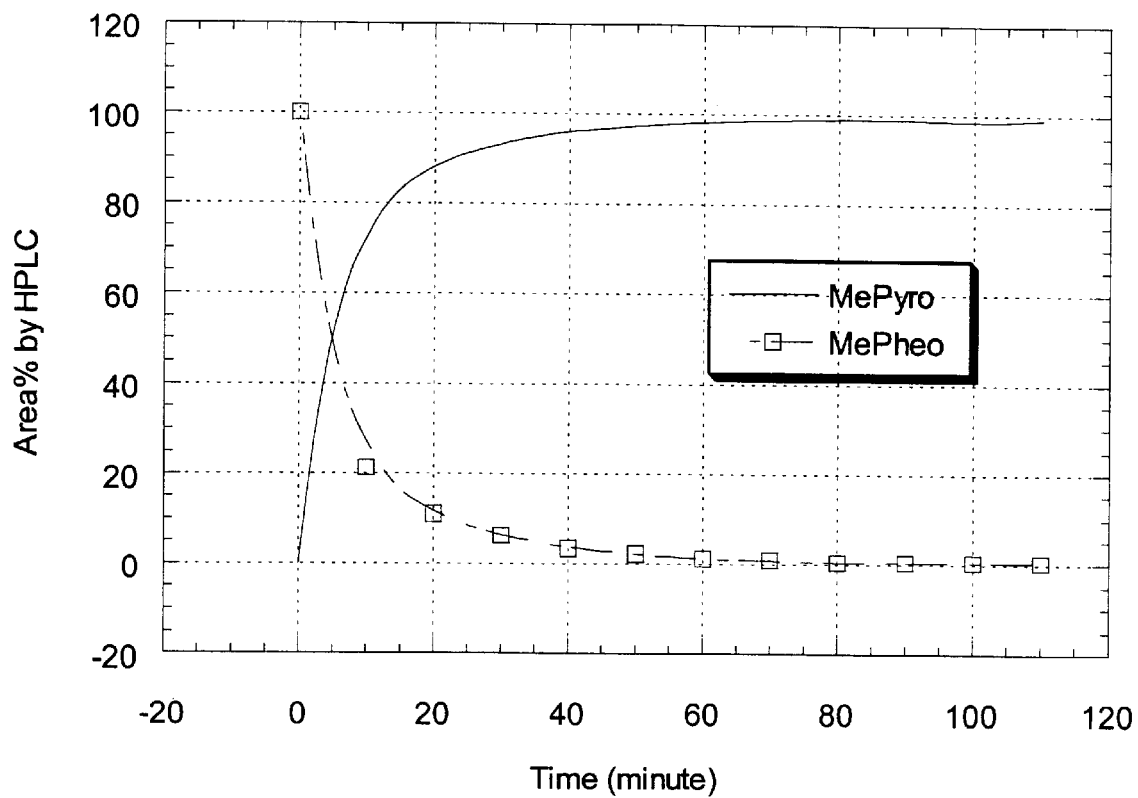
Figure 2. Demethoxycarbonylation of methyl pheophorbide (100 mg) in DMF*/water (2 equiv.)
* DMF (Burdick & Jacksen) was used as is.

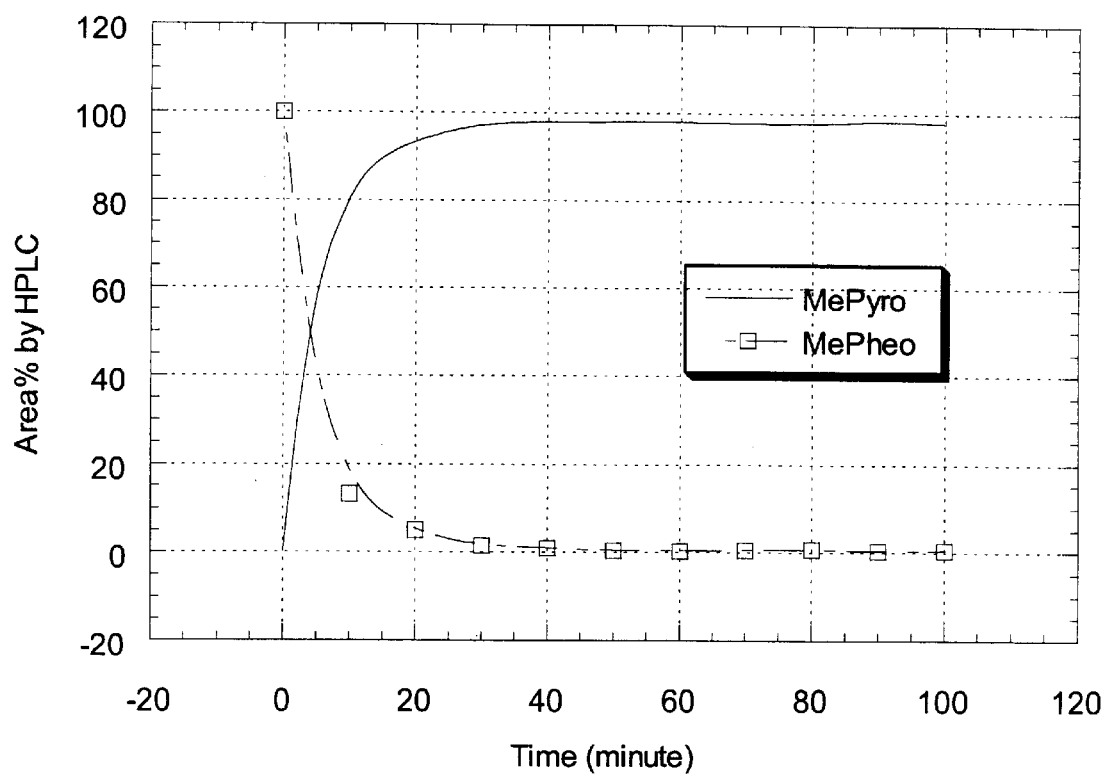
Figure 3. Demethoxycarbonylation of methyl pheophorbide (100 mg) in DMF*/water (16 equiv.)
* DMF (Burdick & Jacksen) was used as is.

Figure 4. Demethoxycarbonylation of methyl pheophorbide (100 mg) in DMF*/water (6 equiv.)/NaCl (1 equiv.)
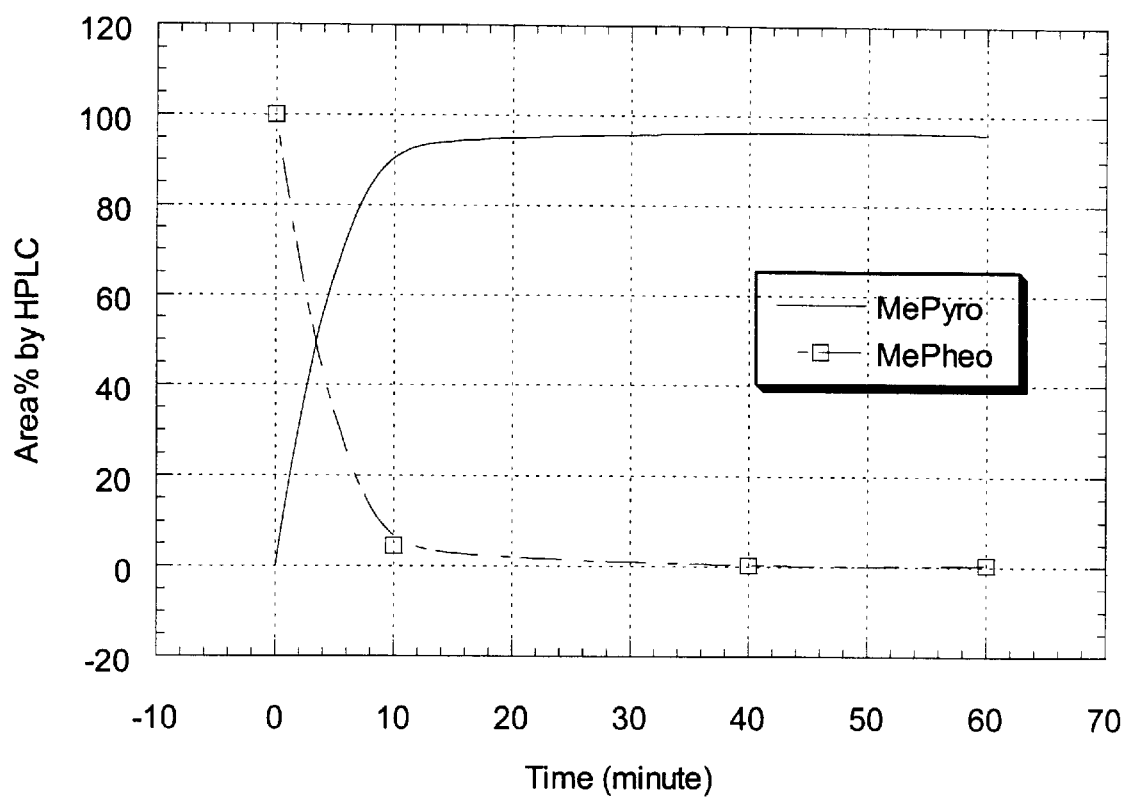
* DMF (Burdick & Jacksen) was used as is.

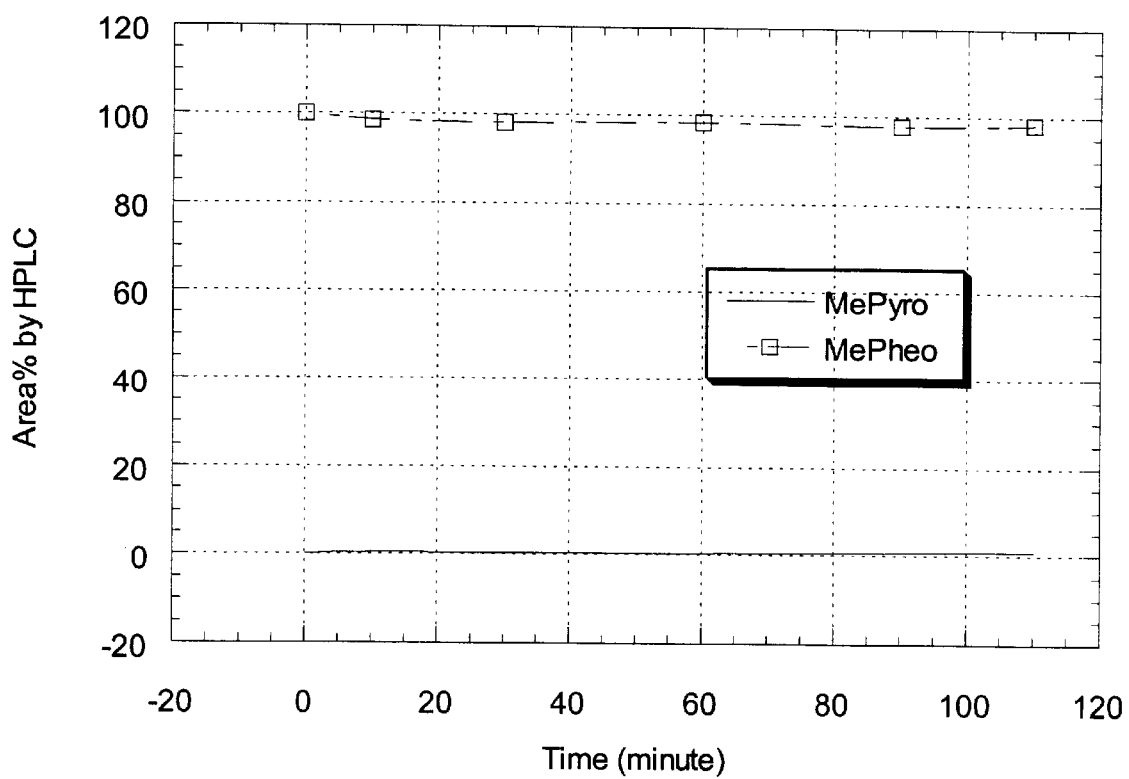
Figure 5. Demethoxycarbonylation of methyl pheophorbide (100 mg) in toluene*/water (2 equiv.)
* Toluene (Fisher) was used as is.

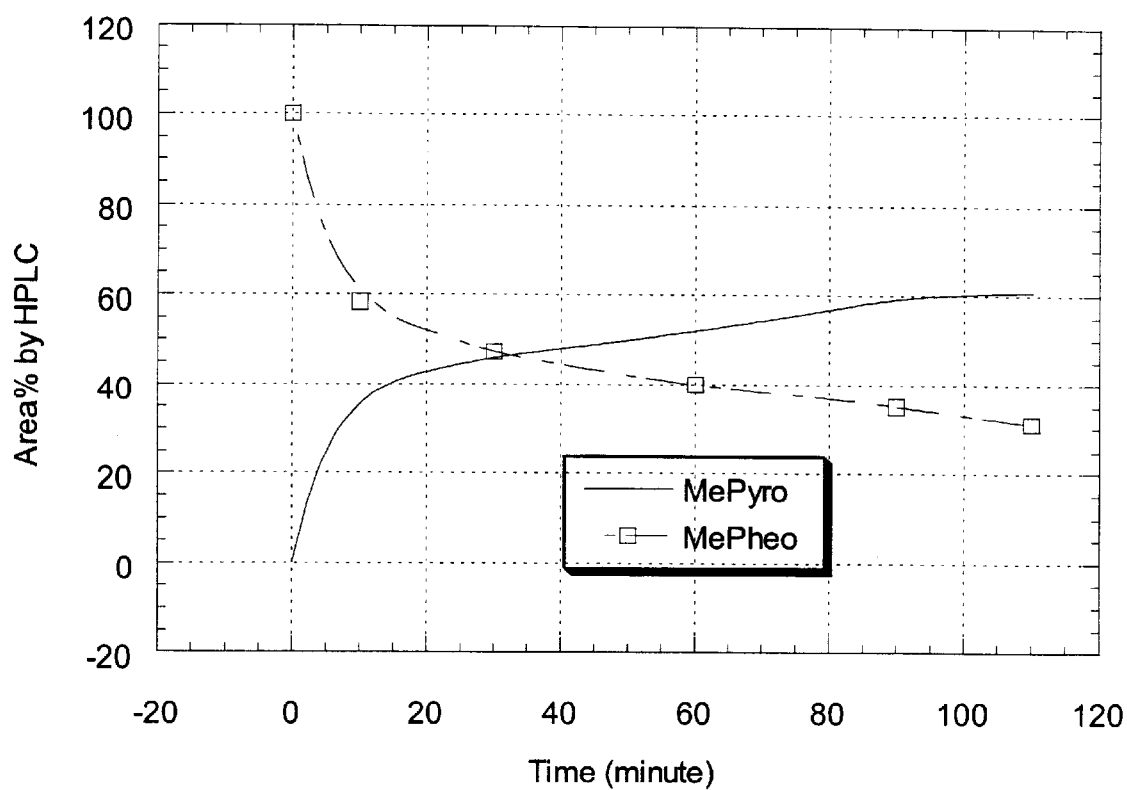
Figure 6. Demethoxycarbonylation of methyl pheophorbide (100 mg) in sec-butylbenzene*/water (4 equiv.)
* sec-Butylbenzene (Aldrich) was used as is.

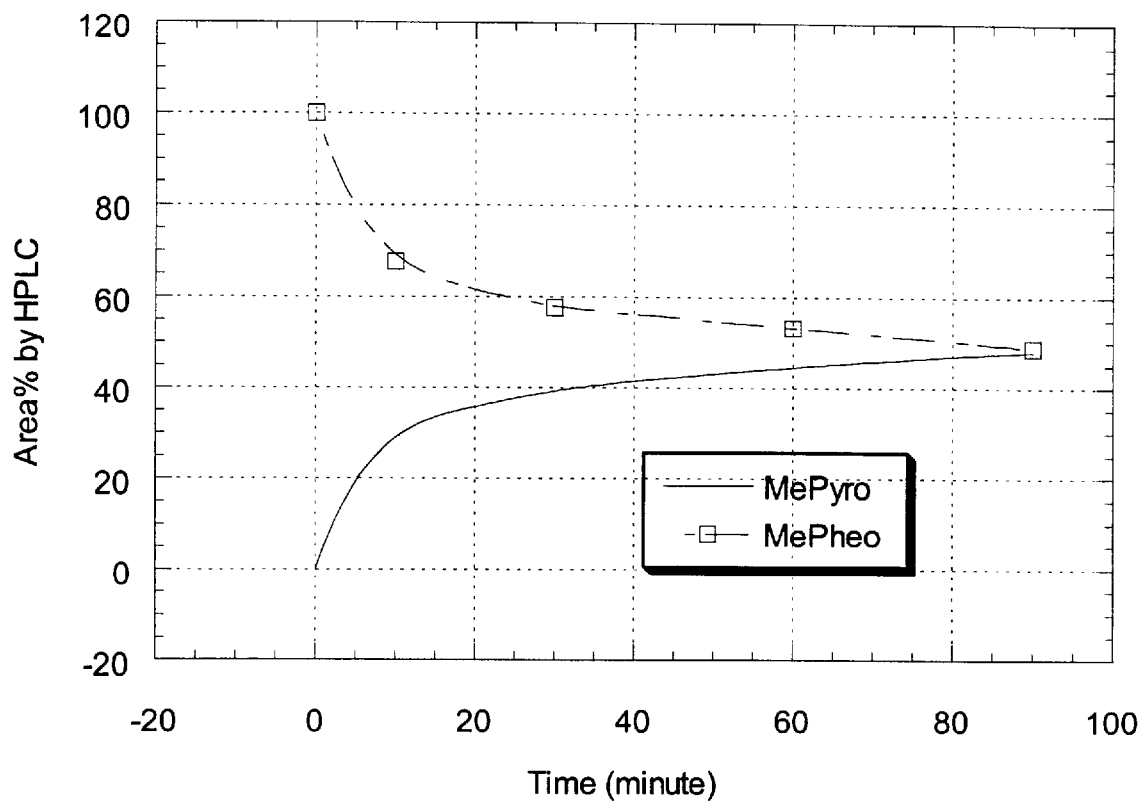
Figure 7. Demethoxycarbonylation of methyl pheophorbide (100 mg) in sec-butylbenzene*/water (16 equiv.)
* sec-Butylbenzene (Aldrich) was used as is.

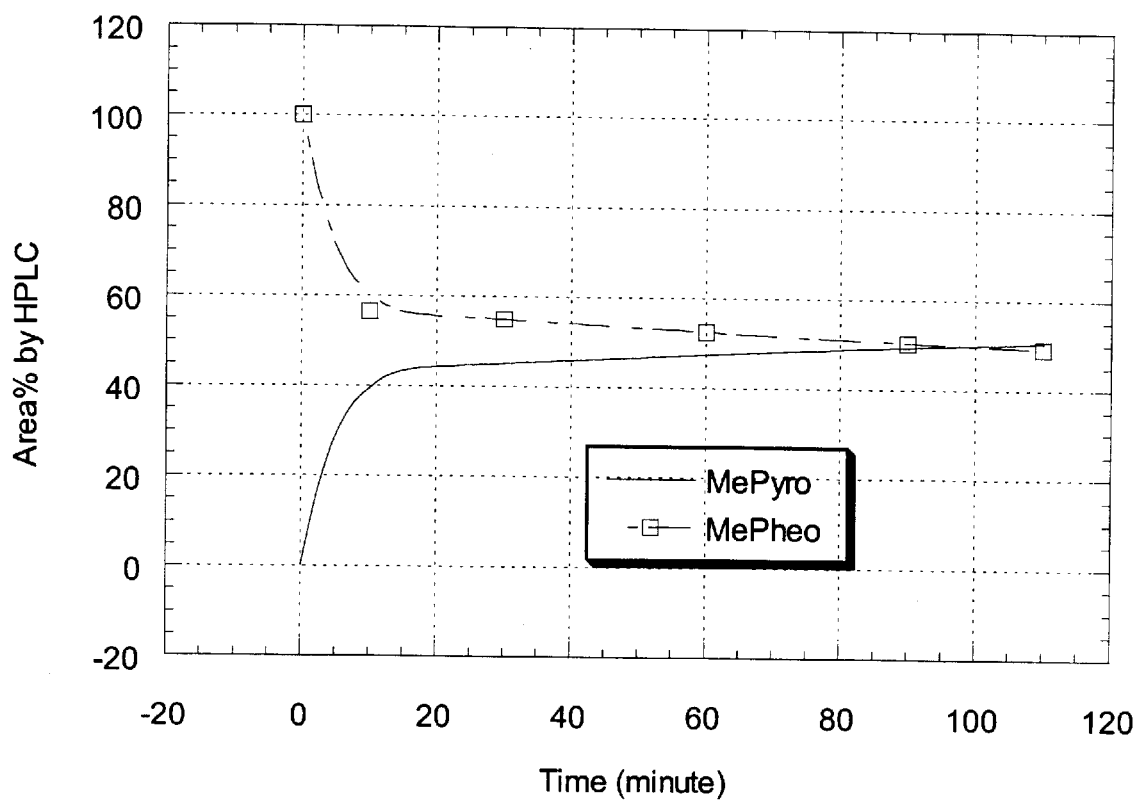
Figure 8. Demethoxycarbonylation of methyl pheophorbide (100 mg) in iodobenzene*/water (16 equiv.)
* Iodobenzene (Aldrich) was used as is.

**Figure 9. Demethoxycarbonylation of methyl pheophorbide (100 mg) in 1-nitropropane*/water (16 equiv.)**
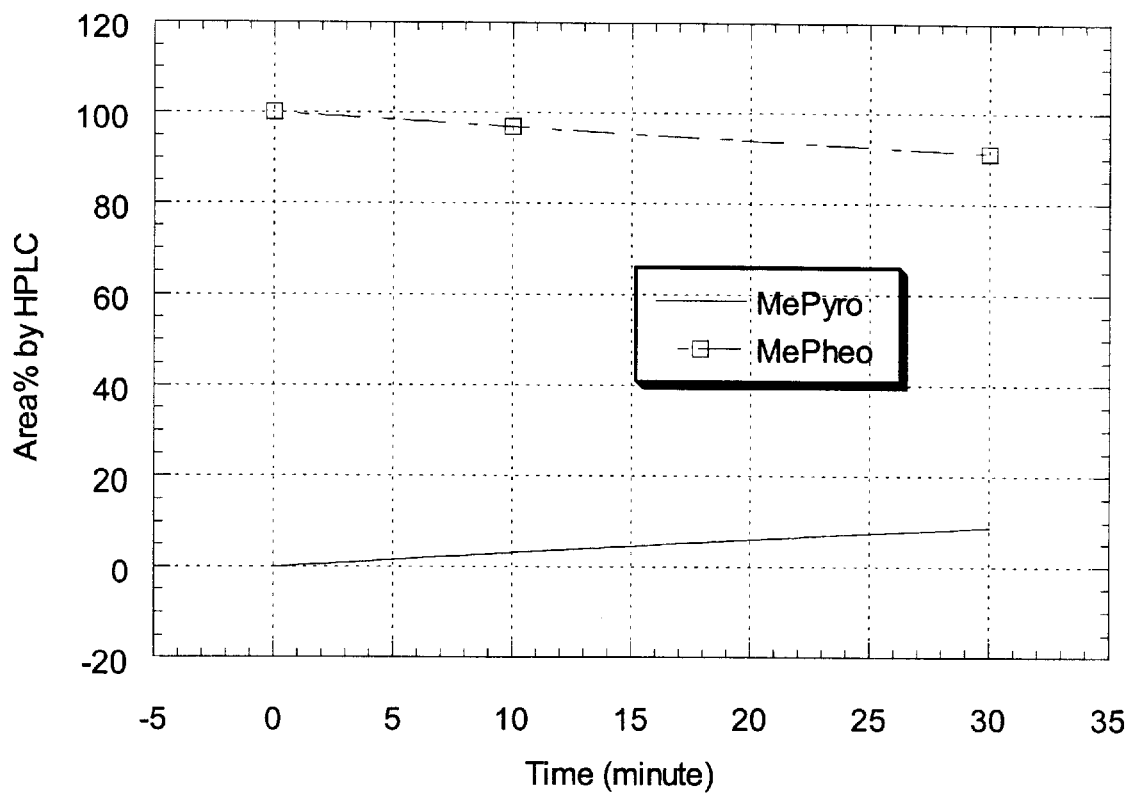
* 1-Nitropropane (Aldrich) was used as is.

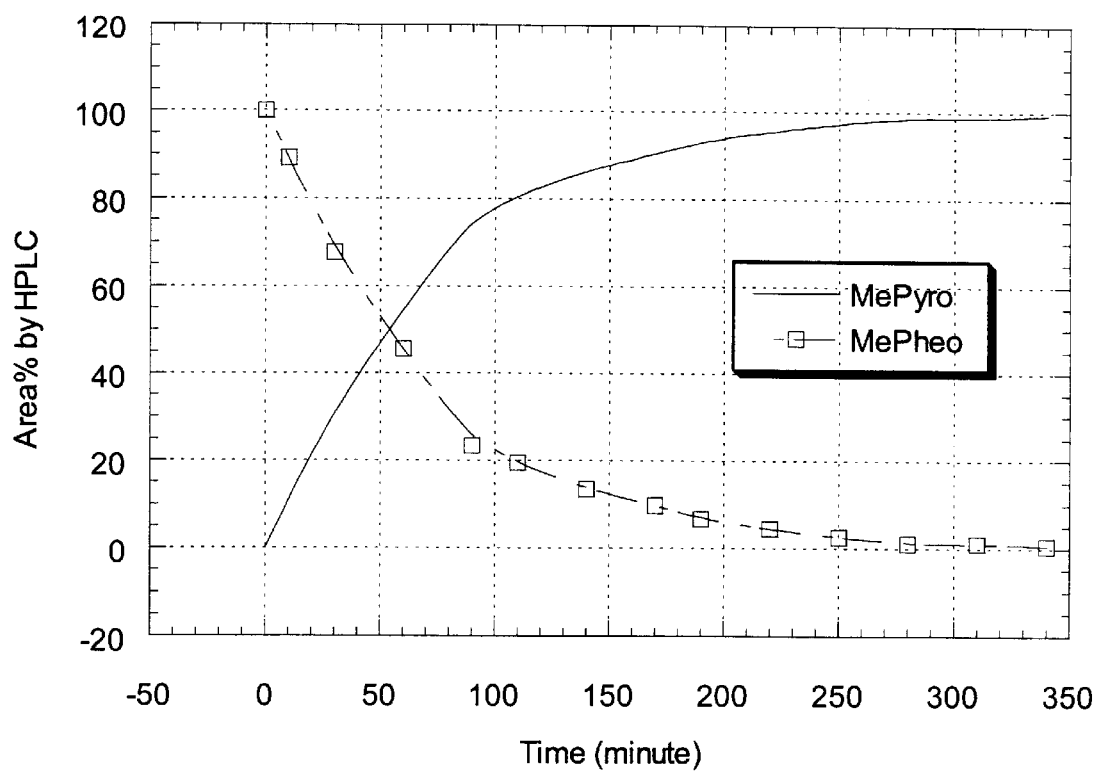
Figure 10. Demethoxycarbonylation of methyl pheophorbide (100 mg) in pyridine*/water (16 equiv.)
* Pyridine (Fisher) was used as is.

Figure 11. Demethoxycarbonylation of methyl pheophorbide (100 mg) in 2,6-lutidine*/water (16 equiv.)
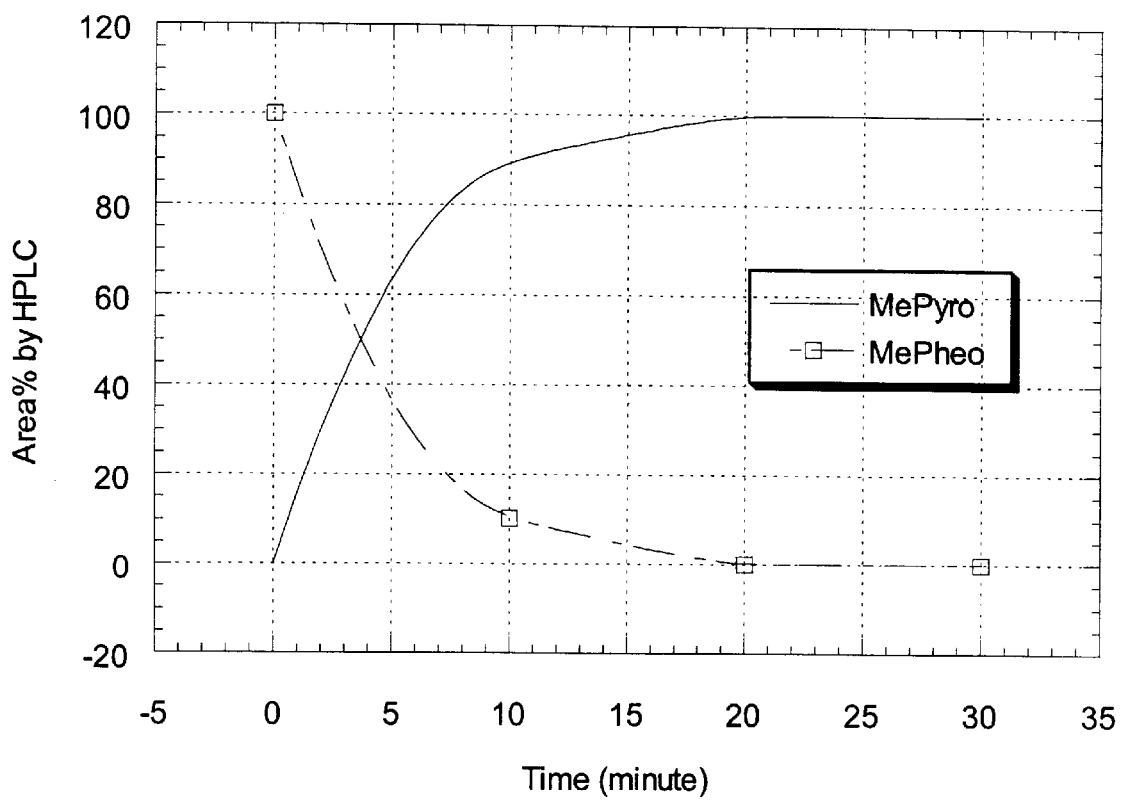
* 2,6-Lutidine (Aldrich) was used as is.

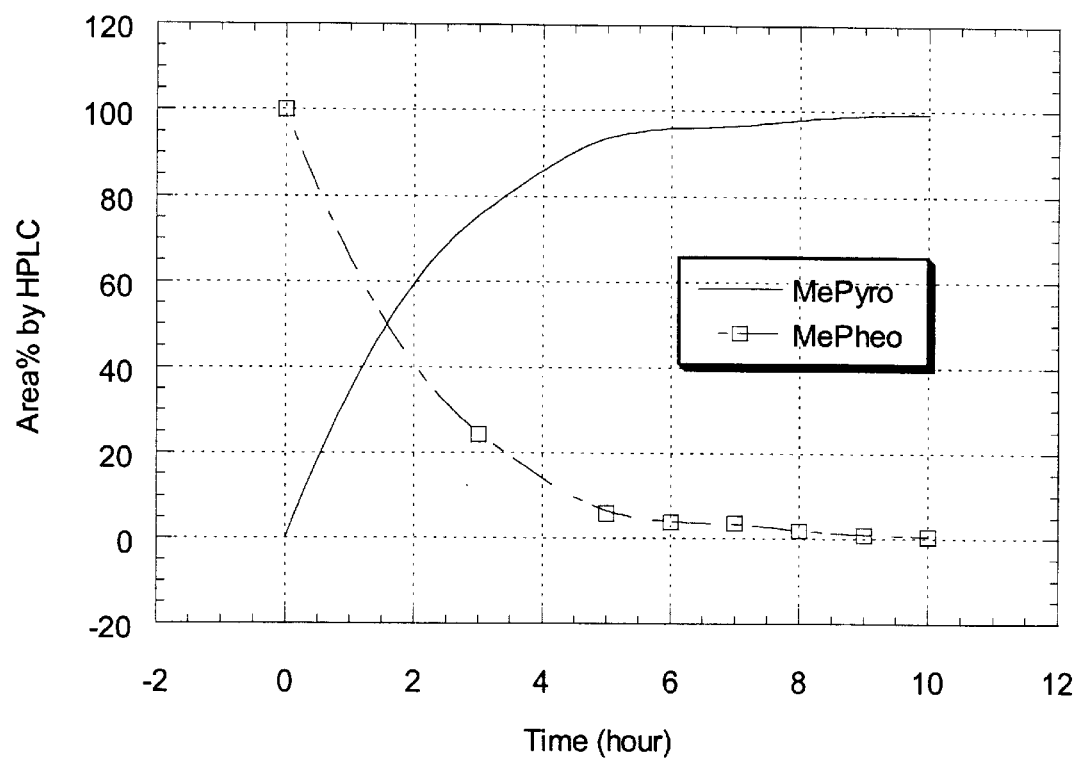
Figure 12. Demethoxycarbonylation of methyl pheophorbide (25 g) in pyridine*/water (13 equiv.)
* Pyridine (Fisher) was used as is.

Figure 13. Demethoxycarbonylation of methyl pheophorbide (100 mg) in pyridine*/water (327 equiv.)
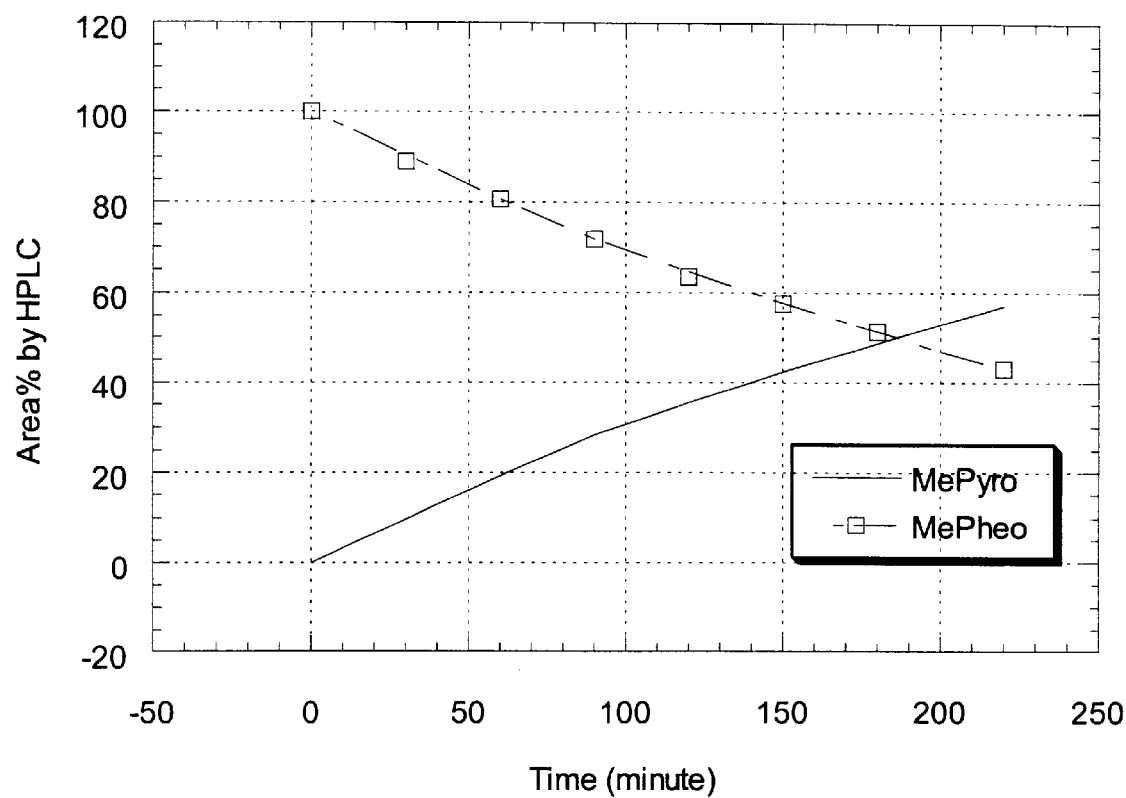
* Pyridine (Fisher) was used as is.

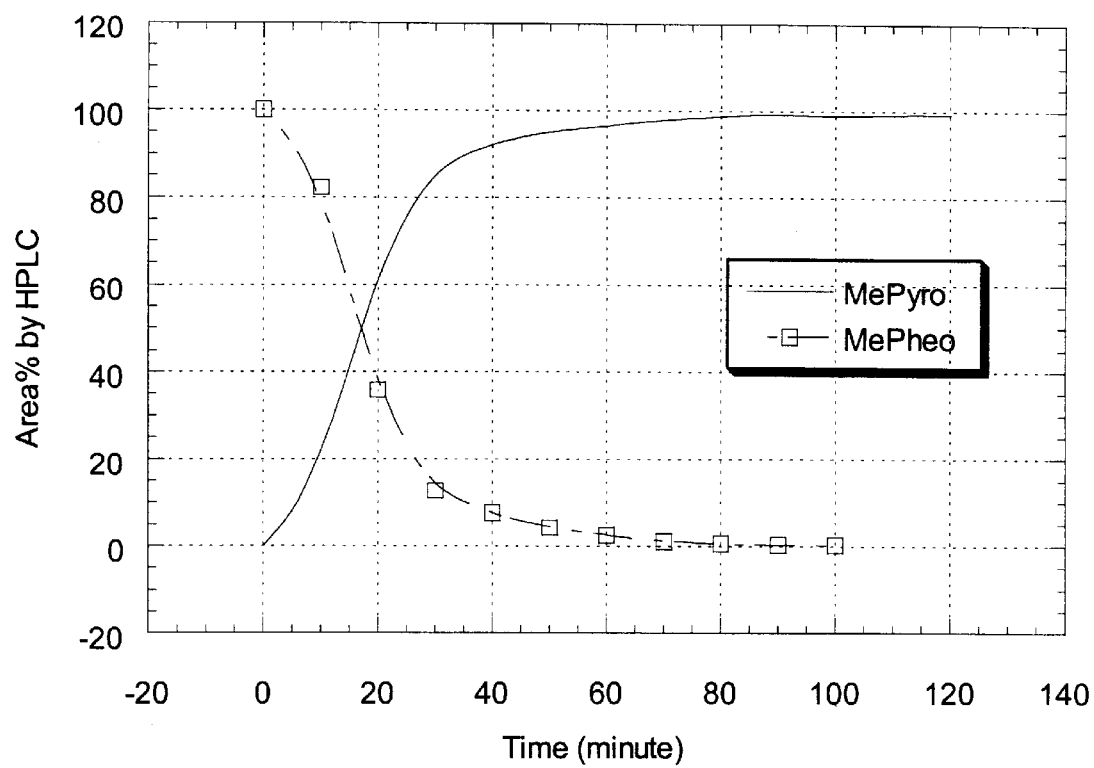
Figure 14. Demethoxycarbonylation of methyl pheophorbide (25 g) in 2,6-lutidine*/water (13 equiv.)
* 2,6-Lutidine (Aldrich) was used as is.

**Figure 15. Demethoxycarbonylation of methyl pheophorbide (100 mg) in 2-picoline*/water (16 equiv.)**
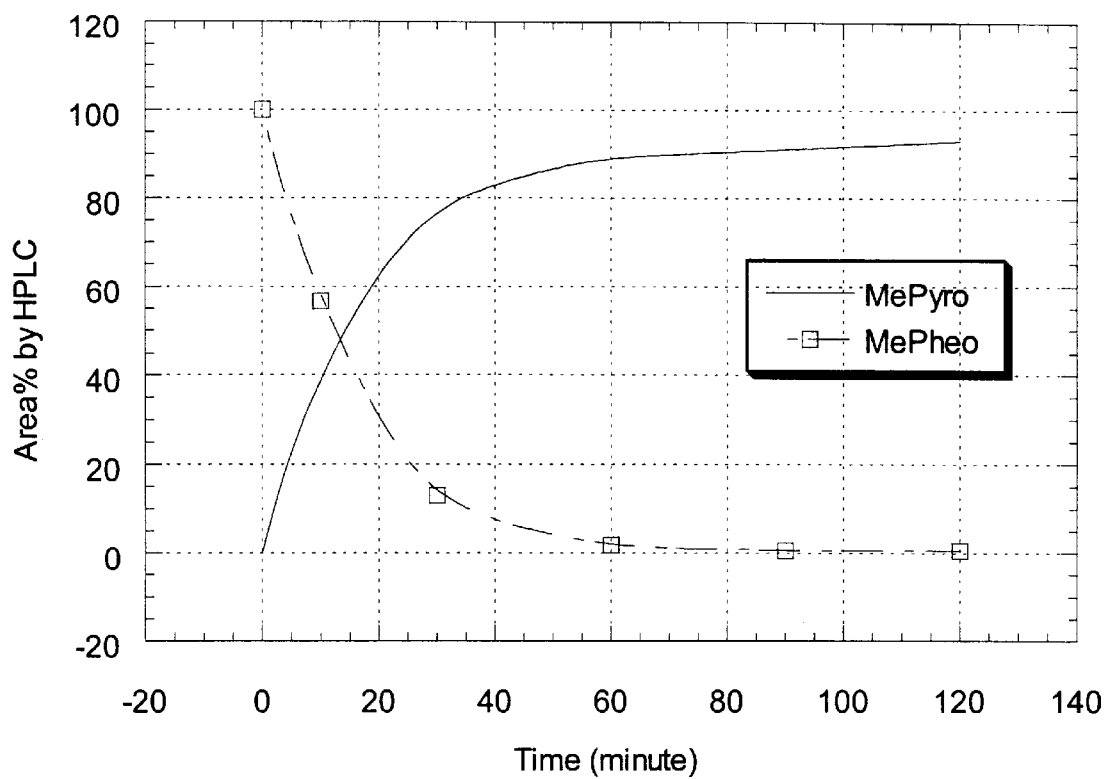
* 2-Picoline (Aldrich) was used as is.

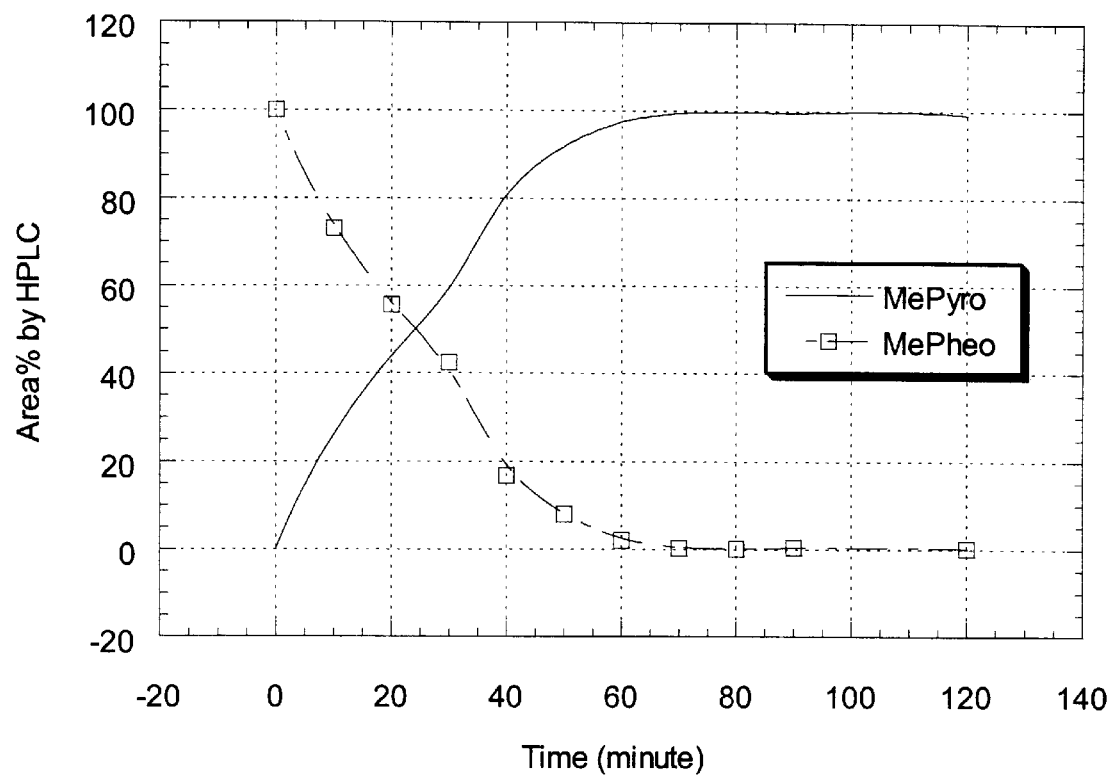
Figure 16. Demethoxycarbonylation of methyl pheophorbide (100 g) in 2,6-lutidine*/water (13 equiv.)
* 2,6-Lutidine (Acros) was used as is.

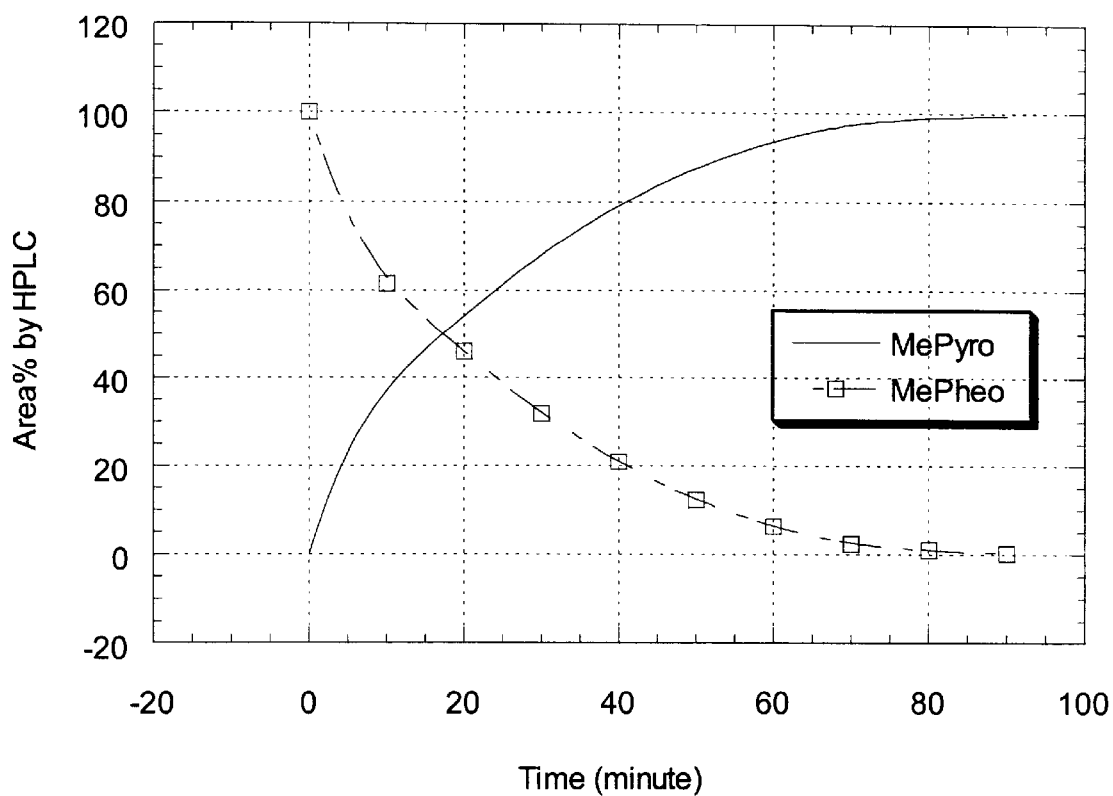
Figure 17. Demethoxycarbonylation of methyl pheophorbide (100 mg) in distilled collidine*/water (327 equiv.)
* Collidine was distilled and stored over molecular sieves (4A) in a round bottom flask sealed by a glass stopper.

Figure 18. Demethoxycarbonylation of methyl pheophorbide (100 mg) in distilled collidine*
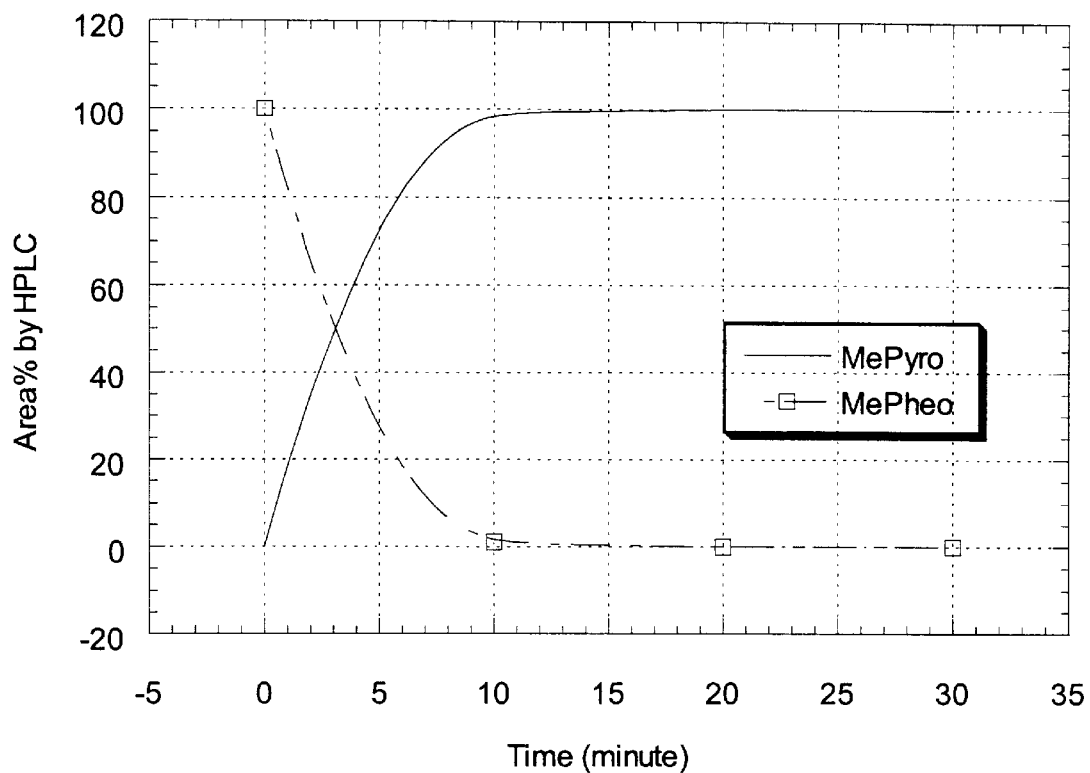
* Collidine was distilled and stored over molecular sieves (4A) in a round bottom flask sealed by a glass stopper.

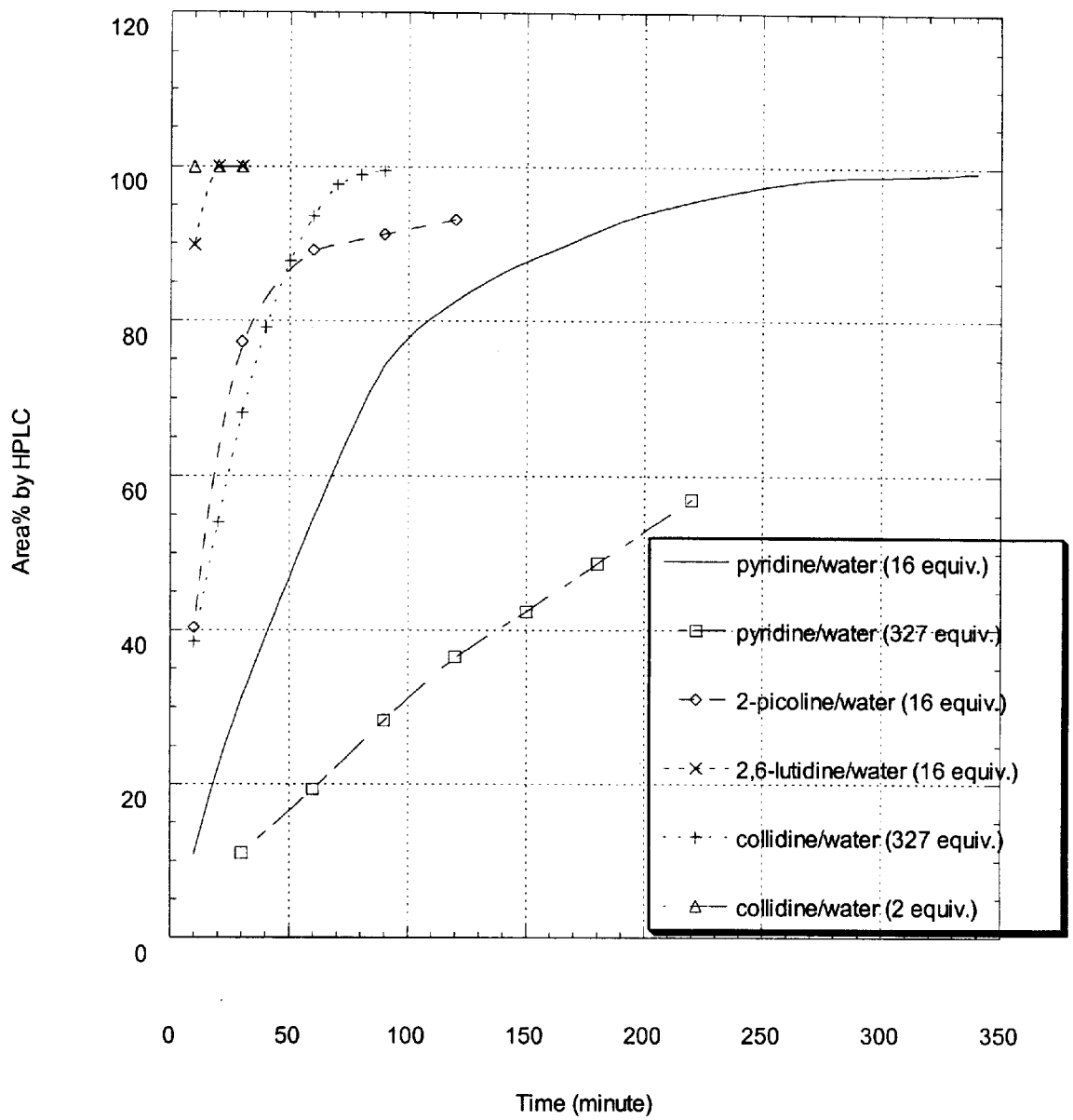
Figure 19. Summary of demethoxycarbonylation of methyl pheophorbide (100 mg) in various pyridine derivatives

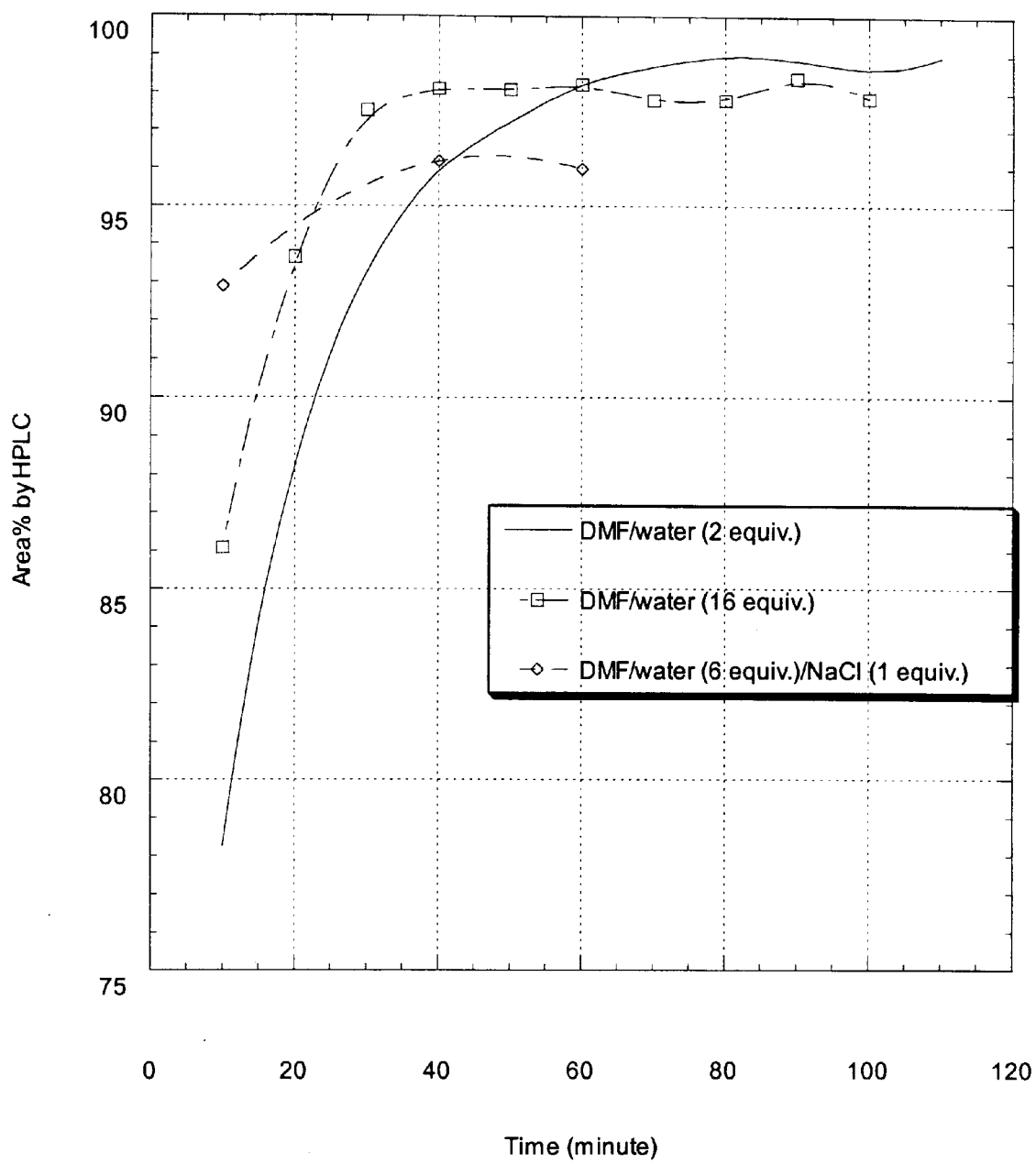
Figure 20. Summary of demethoxycarbonylation of methyl pheophorbide (100 mg) in various DMF/water conditions

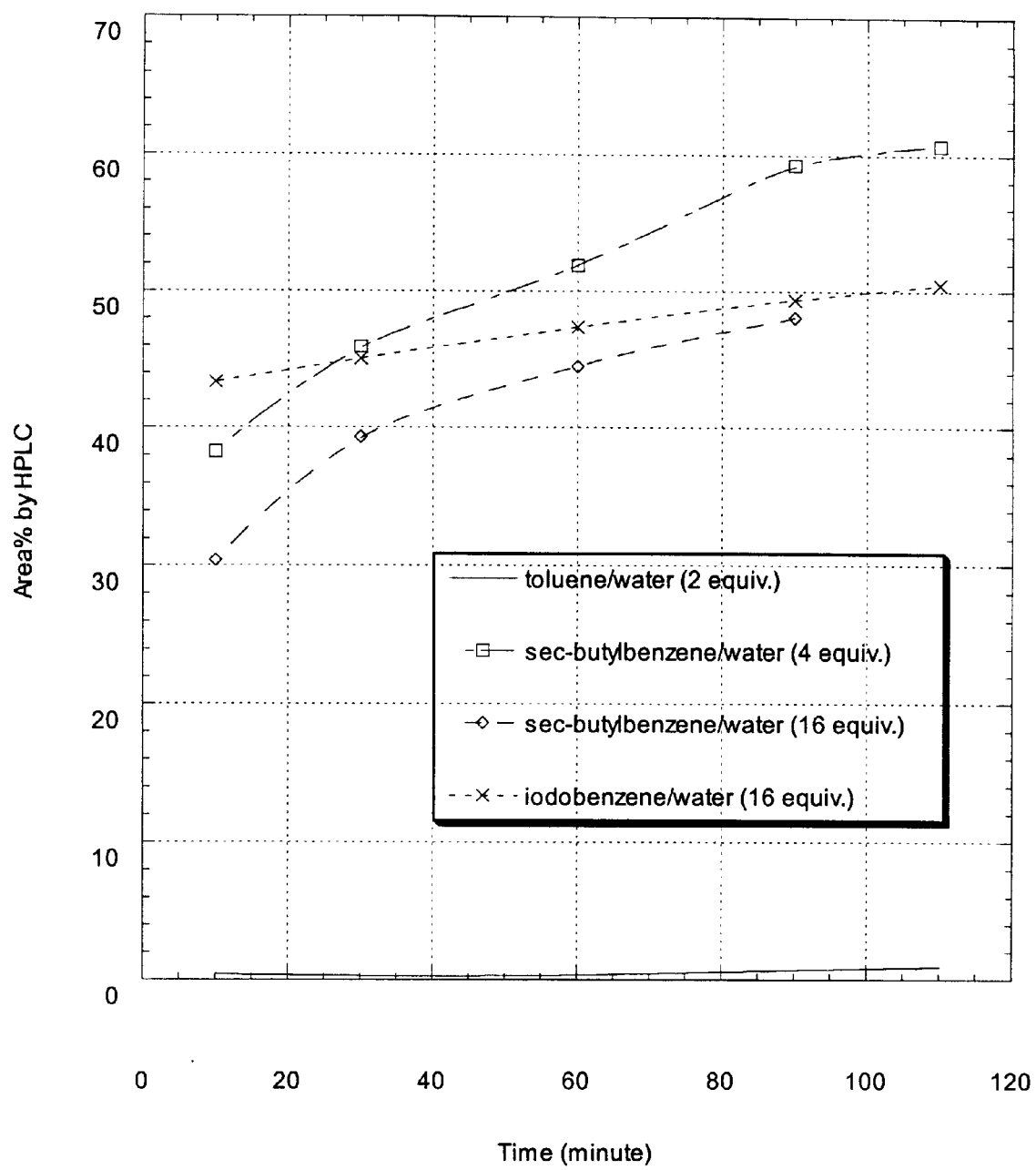
Figure 21. Summary of demethoxycarbonylation of methyl pheophorbide (100 mg) in various benzene derivatives

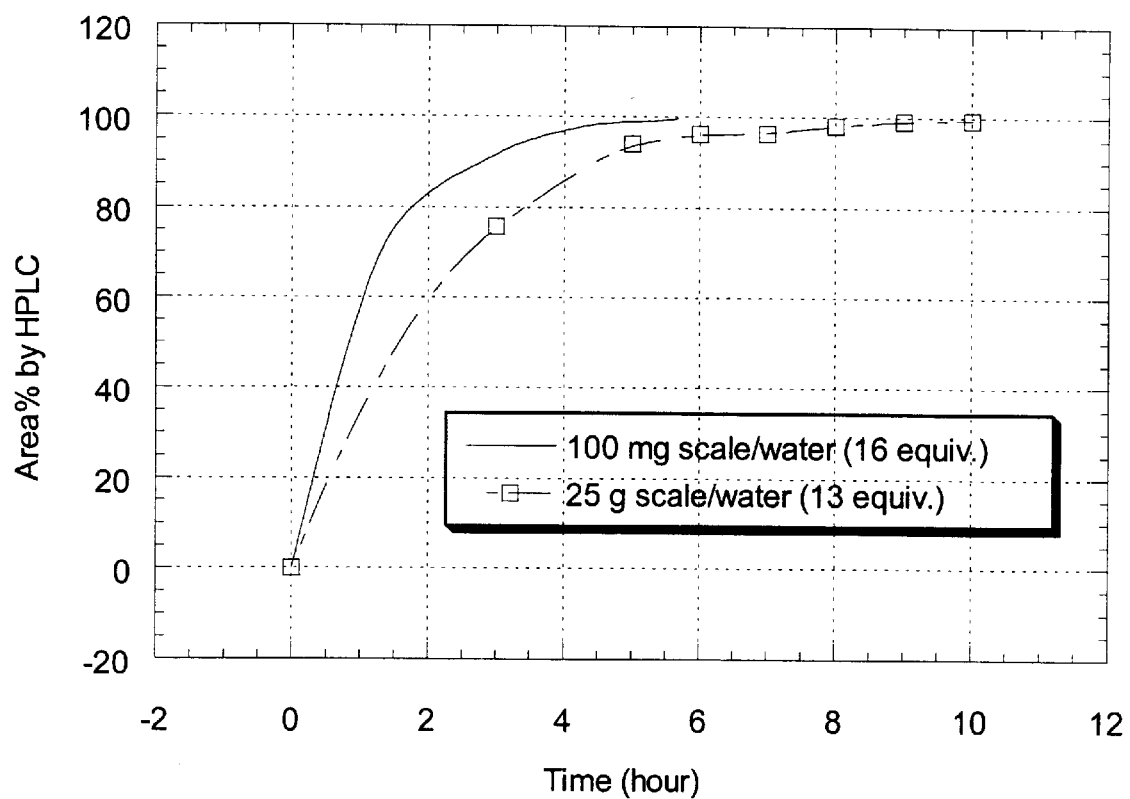
Figure 22. Summary of demethoxycarbonylation of methyl pheophorbide (100 mg and 25 g) in pyridine/water

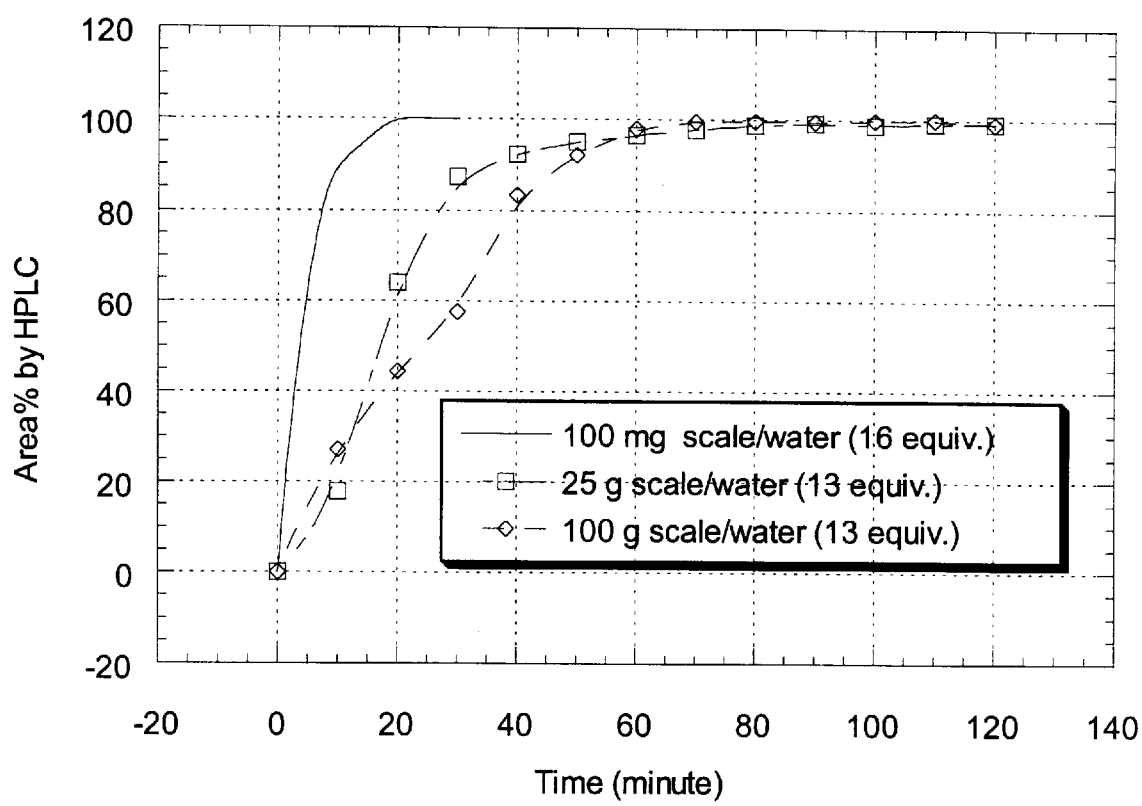
Figure 23. Summary of demethoxycarbonylation of methyl pheophorbide (100 mg, 25 g and 100 g) in 2,6-lutidine/water

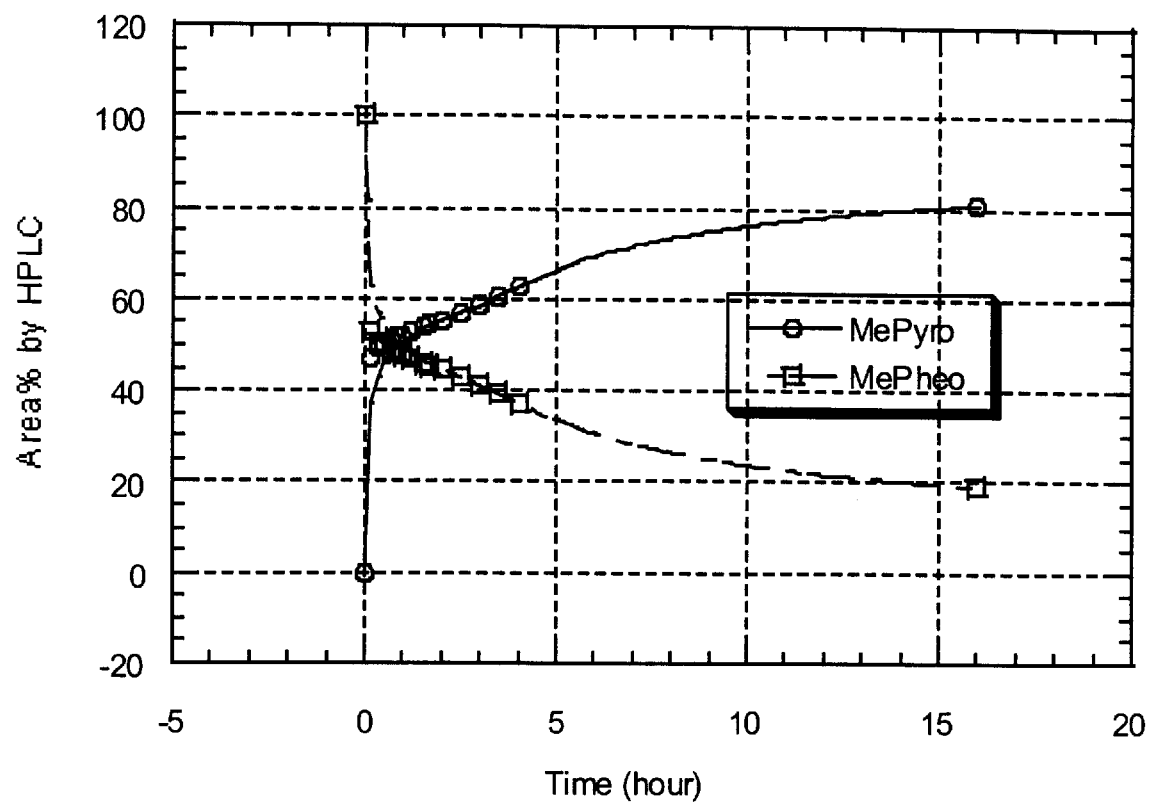
Figure 24. Demethoxycarbonylation of methyl pheophorbide (2 g) in collidine*
* Collidine (Aldrich) was used as is.

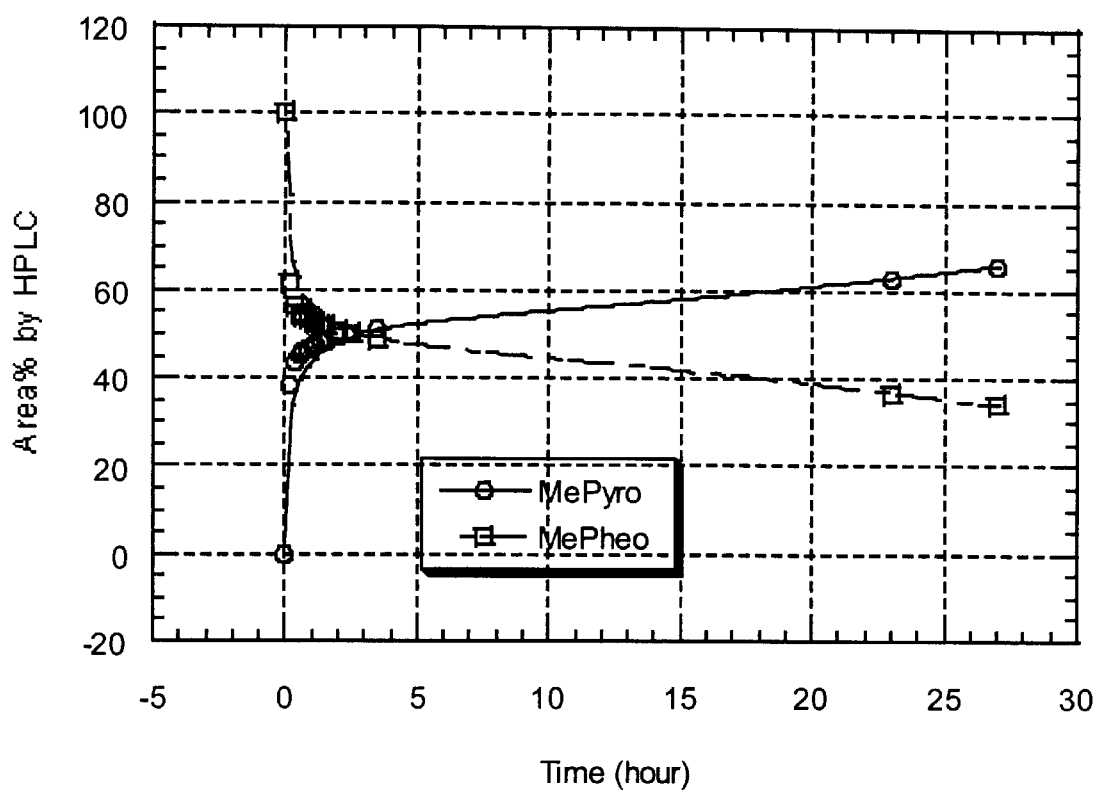
Figure 25. Demethoxycarbonylation of methyl pheophorbide (2 g) in 2,6-lutidine*
* 2,6-Lutidine (Acros) was used as is.

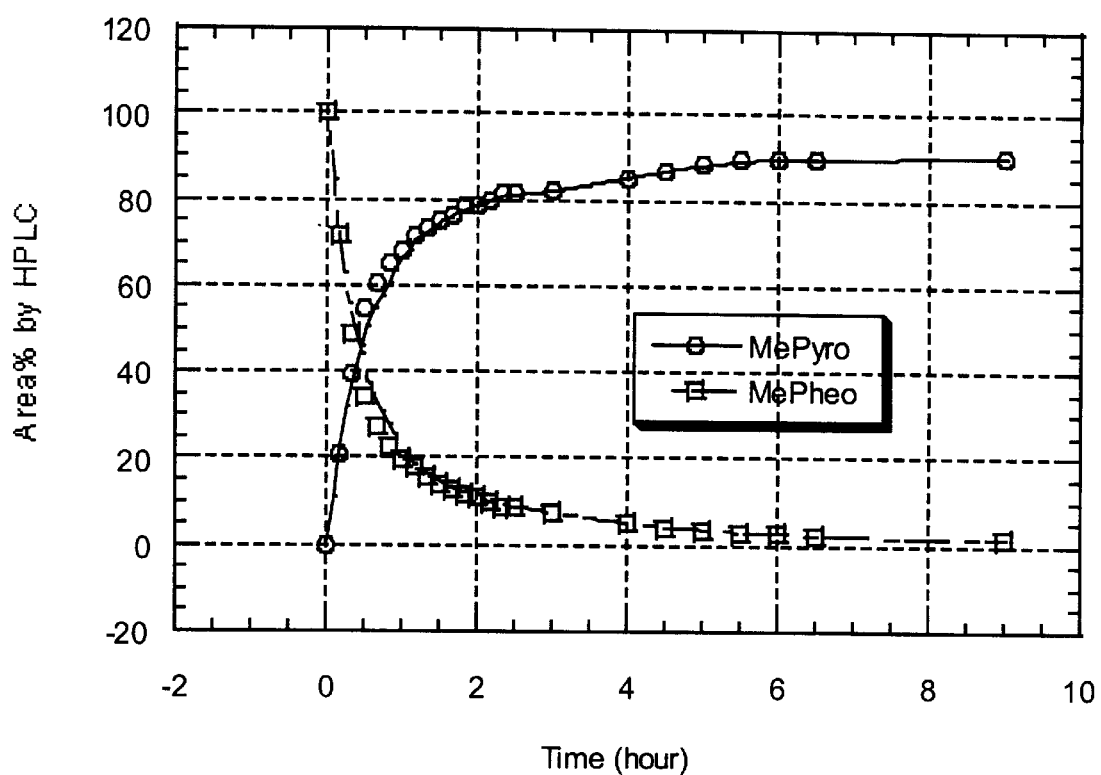
Figure 26. Demethoxycarbonylation of methyl pheophorbide (2 g) in 2-picoline*
* 2-Picoline (Aldrich) was used as is.

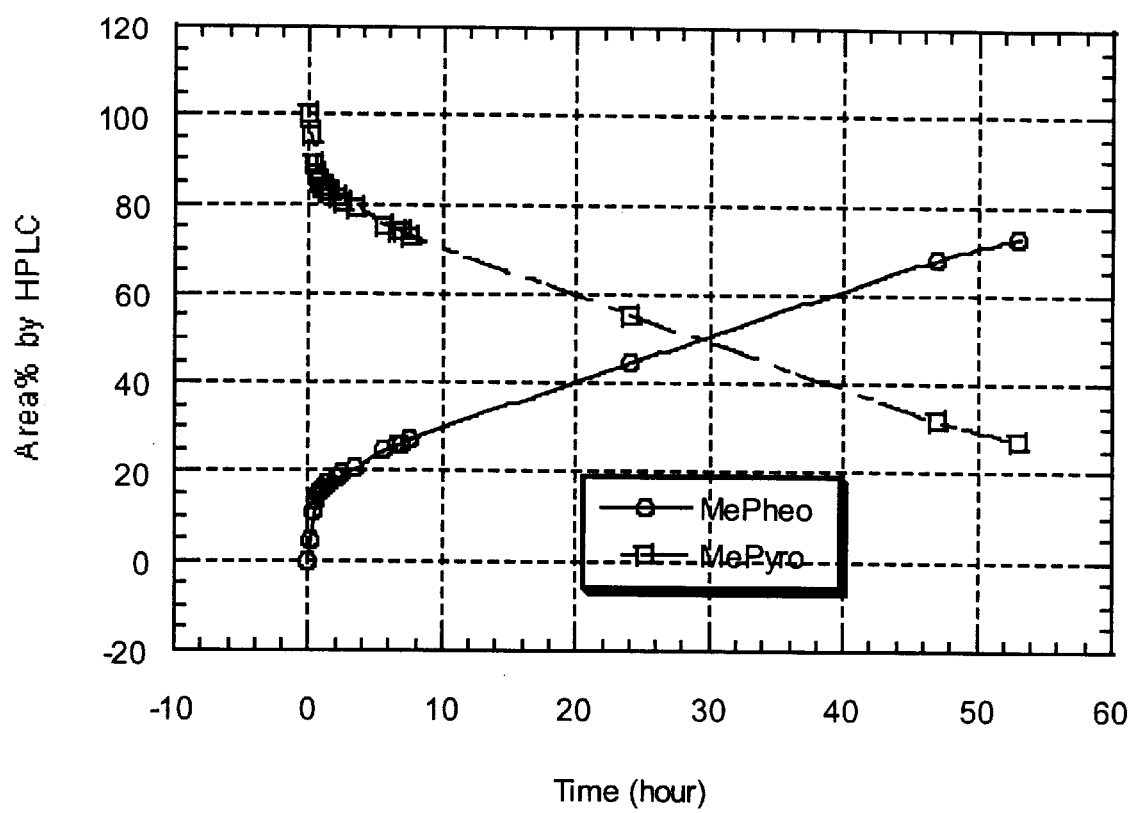
Figure 27. Demethoxycarbonylation of methyl pheophorbide (2 g) in pyridine*
*Pyridine (Aldrich) was used as is.

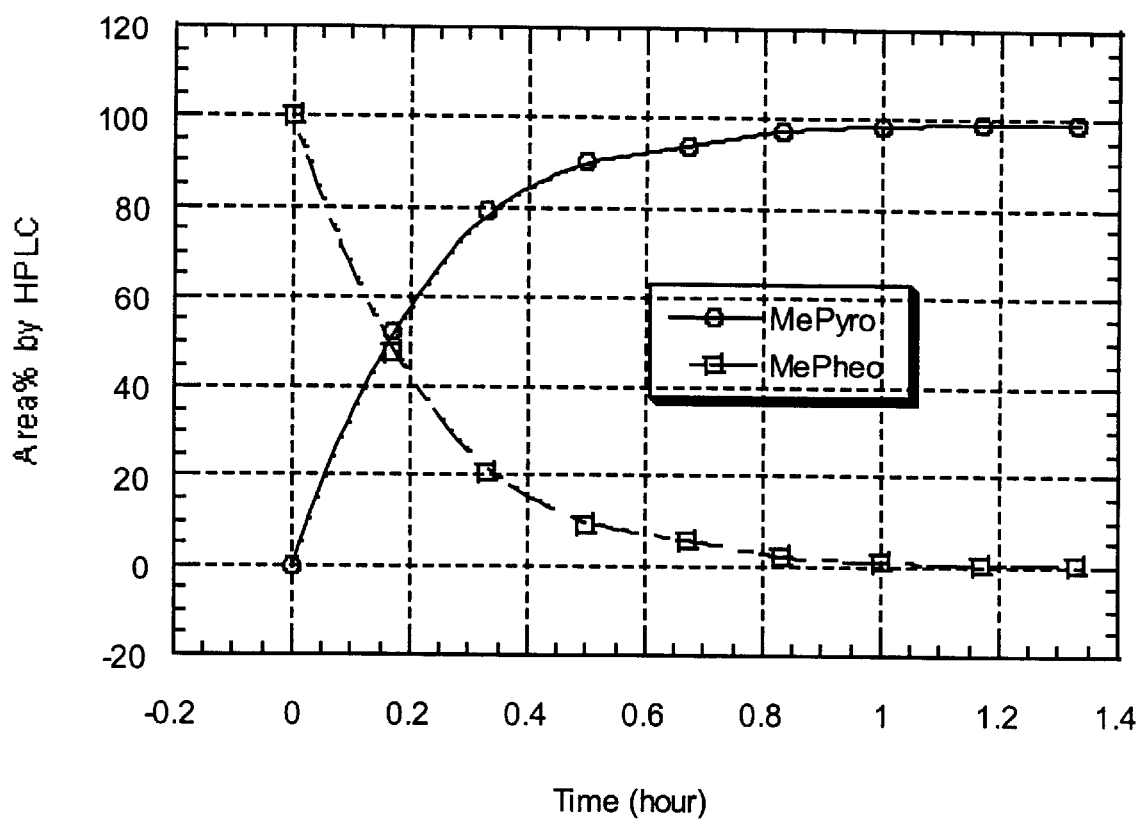
Figure 28. Demethoxycarbonylation of methyl pheophorbide (2 g) in 2,6-lutidine*/water (13 equiv.)
* 2,6-Lutidine (Aldrich) was used as is.

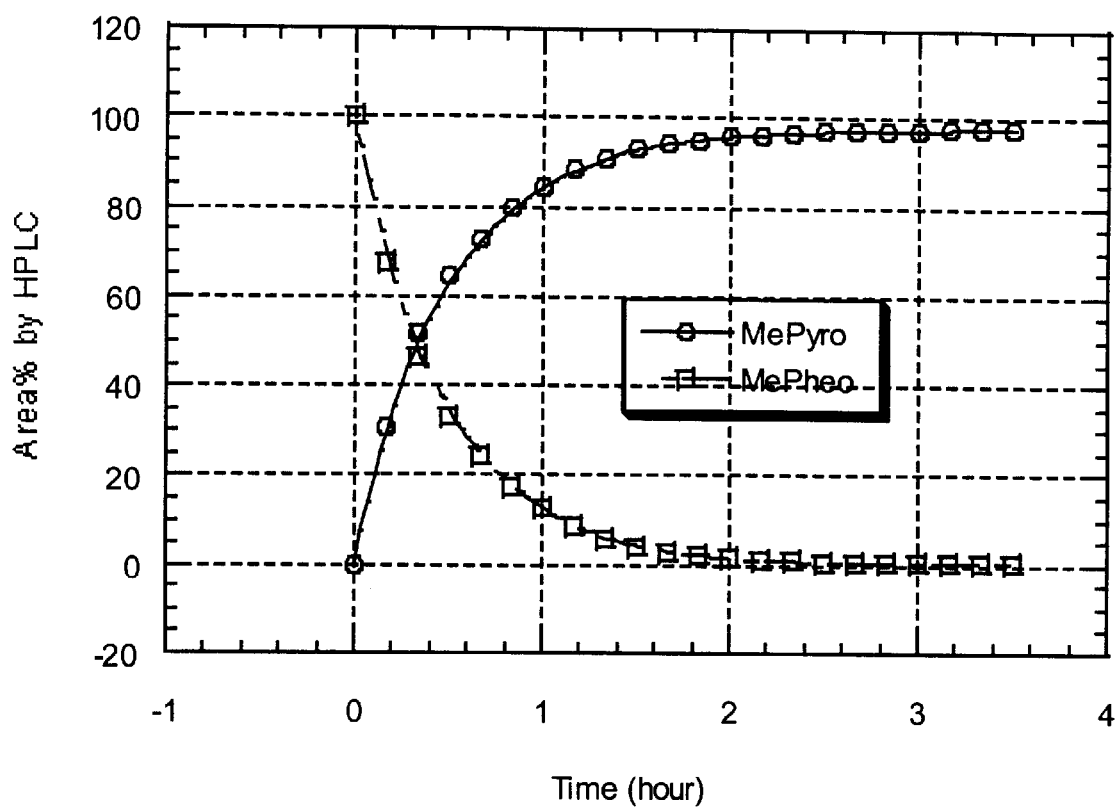
Figure 29. Demethoxycarbonylation of methyl pheophorbide (2 g) in 2-picoline*/water (13 equiv.)
* 2-Picoline (Aldrich) was used as is.

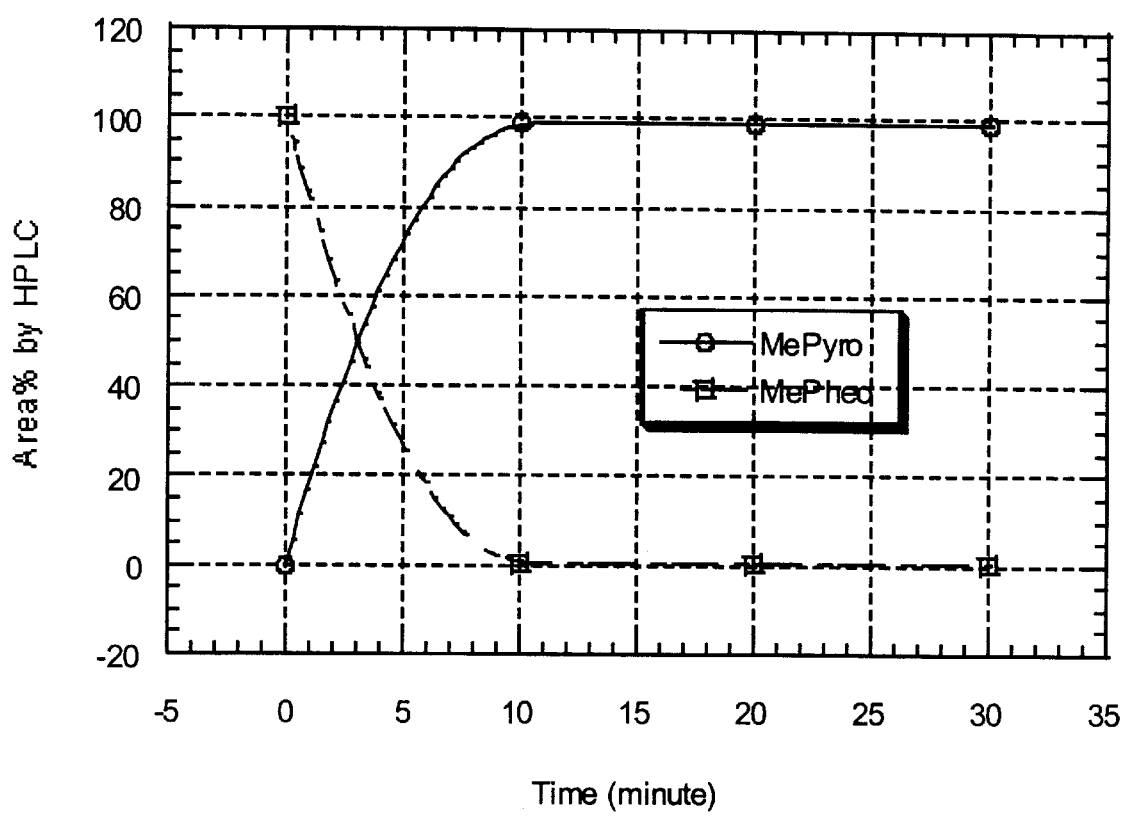
Figure 30. Demethoxycarbonylation of methyl pheophorbide (2 g) in collidine*/water (13 equiv.)
* Collidine (Aldrich lot #: 02201BQ) was used as is.

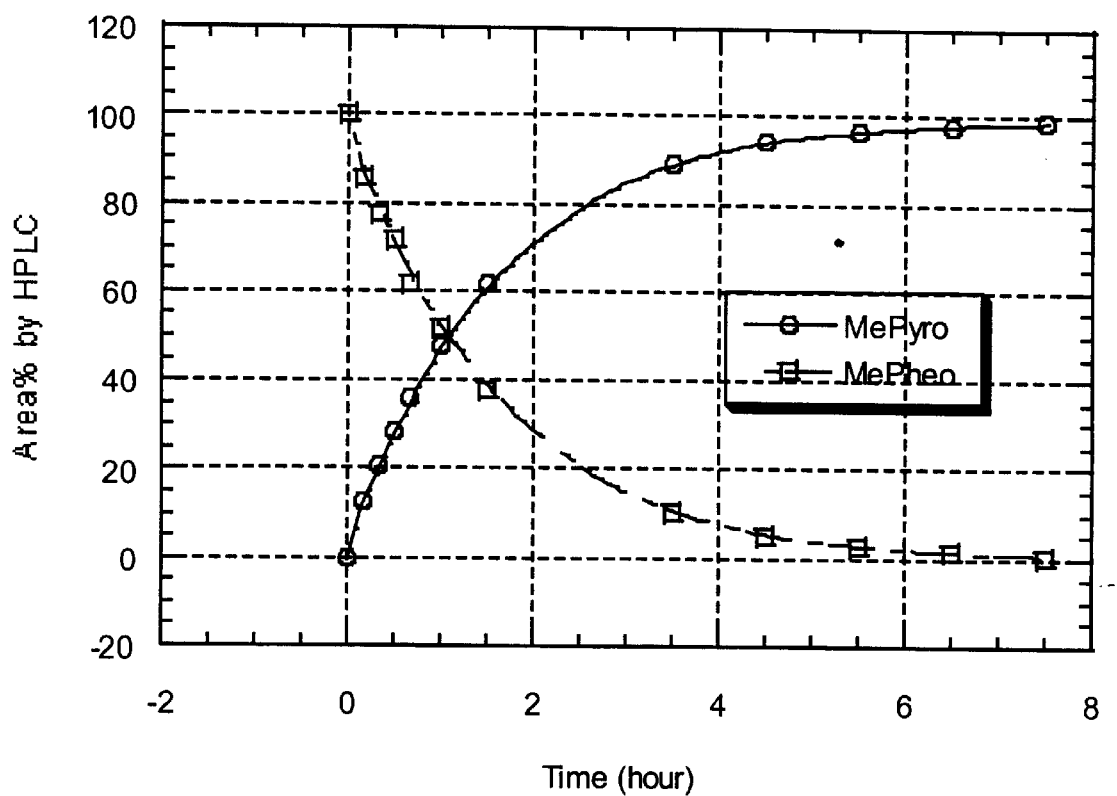
Figure 31. Demethoxycarbonylation of methyl pheophorbide (2 g) in pyridine*/water (13 equiv.)
*Pyridne (Aldrich) was used as is.

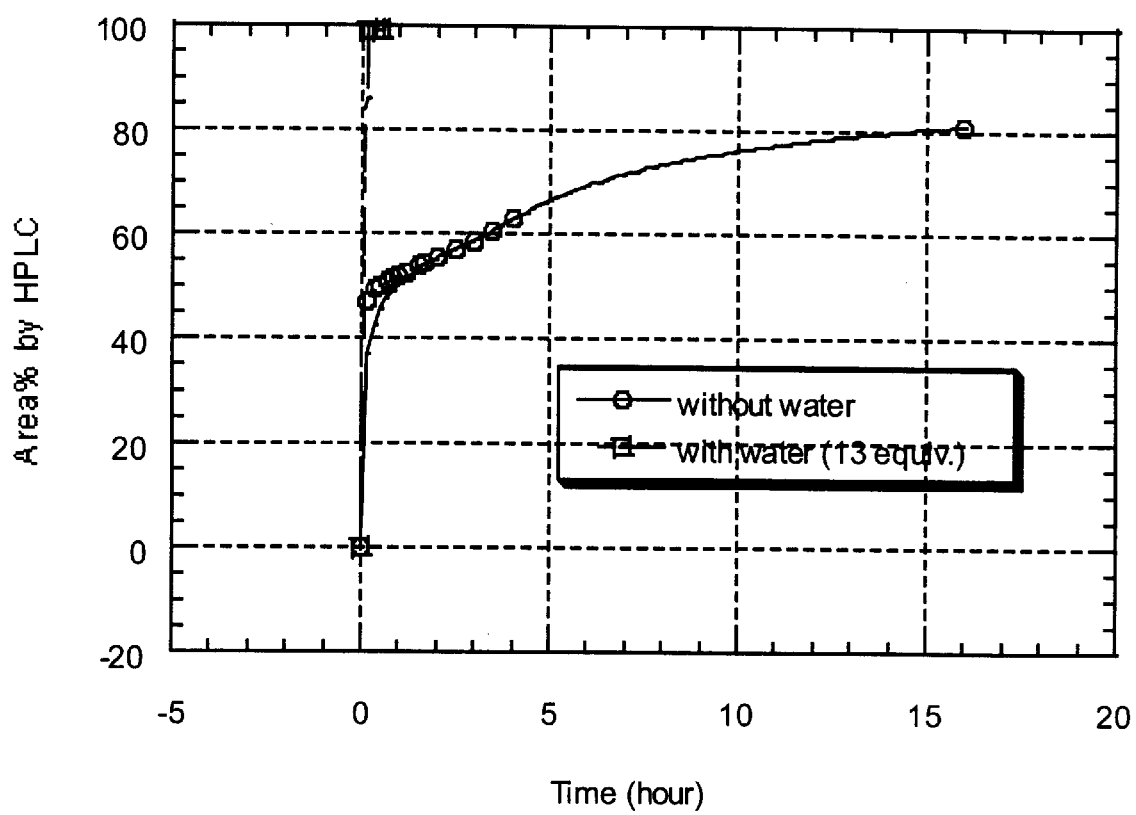
Figure 32. Summary of demethoxycarbonylation of methyl pheophorbide (2 g) in collidine with water (13 equiv.) and without

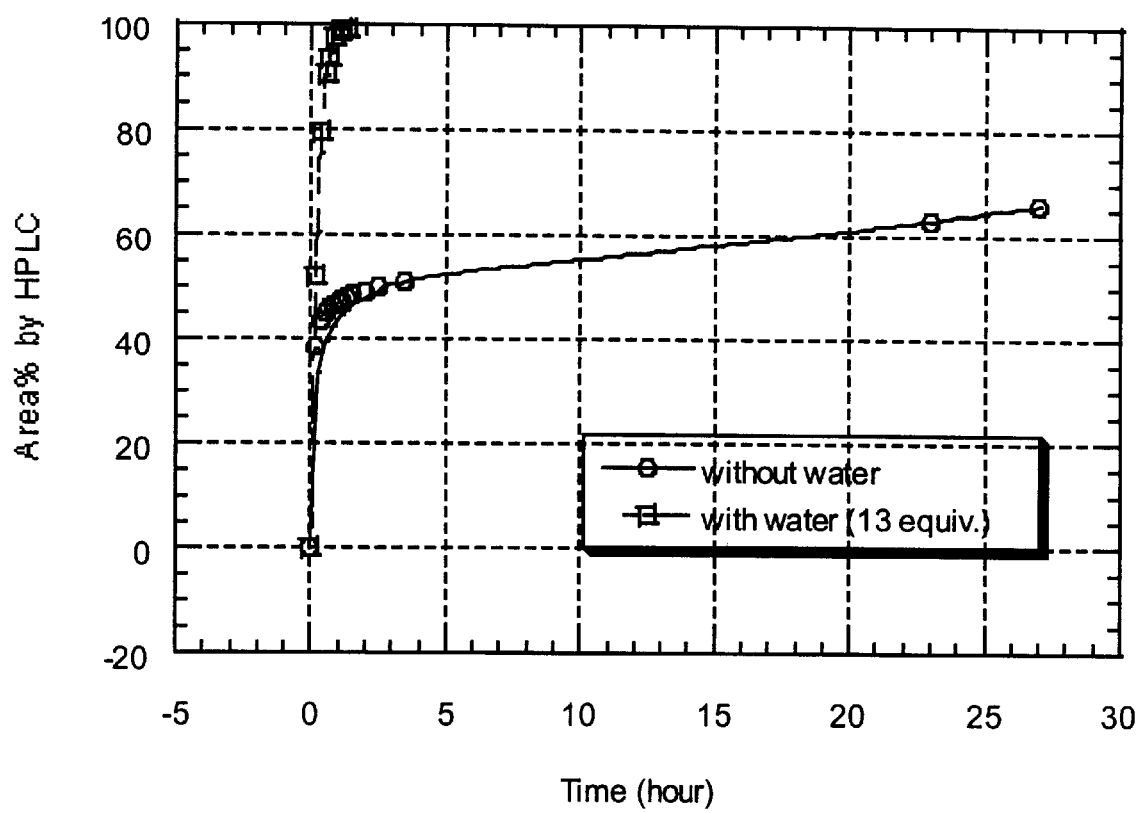
Figure 33. Summary of demethoxycarbonylation of methyl pheophorbide (2 g) in 2,6-lutidine with water (13 equiv.) and without

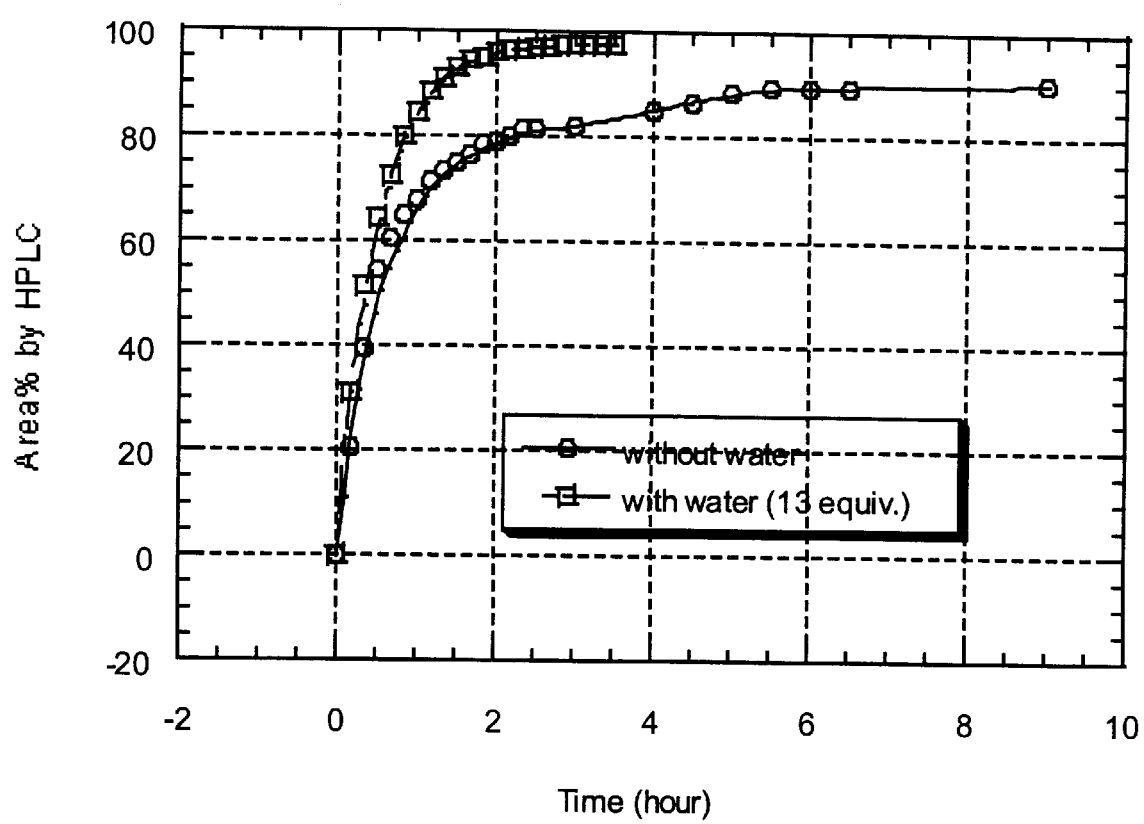
Figure 34. Summary of demethoxycarbonylation of methyl pheophorbide (2 g) in 2-picoline with water (13 equiv.) and without

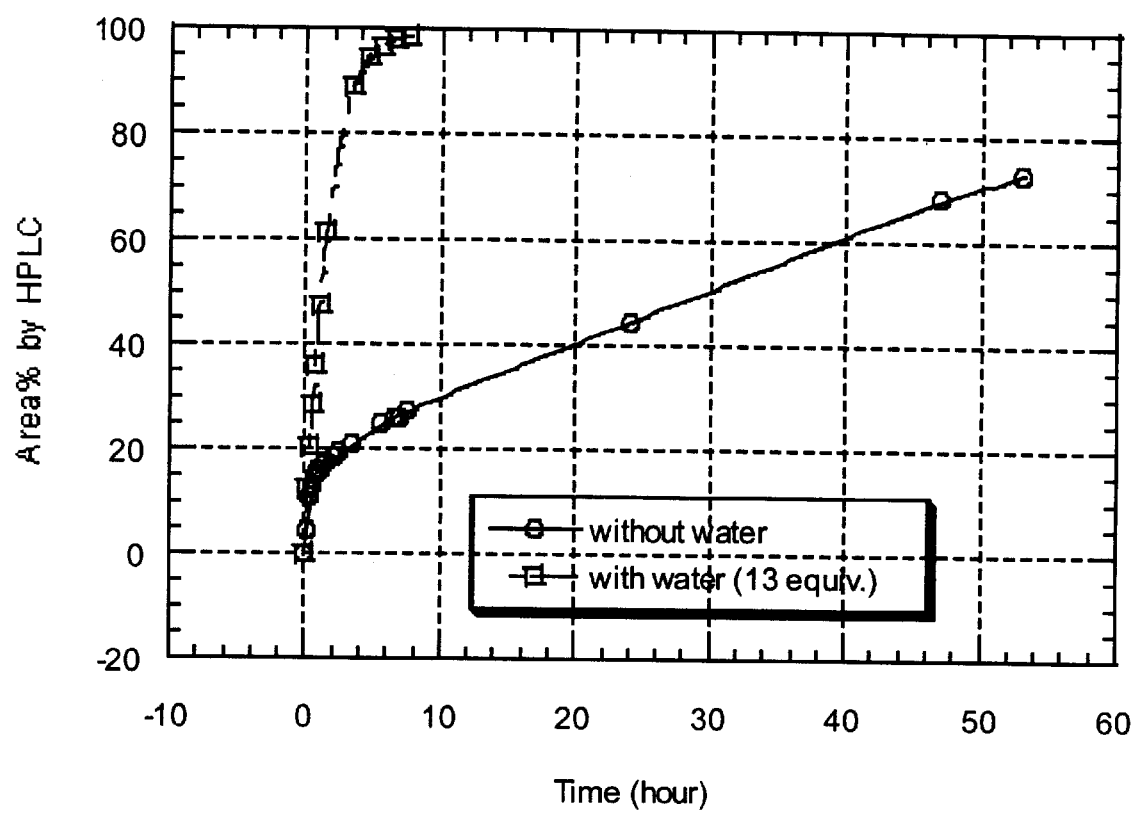
Figure 35. Summary of demethoxycarbonylation of methyl pheophorbide (2 g) in pyridine with water (13 equiv.) and without

METHOD FOR THE DEMETHOXYCARBONYLATION OF PORPHYRINIC COMPOUNDS SUCH AS PHEOPHORBIDES

FIELD OF THE INVENTION

The present invention relates to an improved method for producing porphyrinic compounds such as pheophorbides useful as photoselective compounds in photodynamic therapy.

BACKGROUND OF THE INVENTION

Photodynamic therapy is a procedure that uses photoselective (light-activated) drugs to target and destroy diseased cells. Photoselective drugs transform light energy into chemical energy in a manner similar to the action of chlorophyll in green plants. The photoselective drugs are inactive until switched on by light of a specific wavelength. This gives physicians the potential to target specific groups of cells and control the timing and selectivity of treatment. The result of this process is that diseased cells are destroyed with minimal damage to surrounding normal tissues.

Photodynamic therapy begins with the administration, to a patient, of a photoselective compound that is selectively taken up and/or retained by the biologic target, i.e., tissue or cells. After the photoselective compound is taken up by the target, a light of the appropriate wavelength to be absorbed by the photoselective compound is delivered to the targeted area. This activating light excites the photoselective compound to a higher energy state. The extra energy of the excited photoselective compound can then be used to generate a biological response in the target area. As a result of the irradiation, the photoselective compound exhibits cytotoxic activity, i.e., it destroys cells. By localizing the irradiated area, it is possible to contain the cytotoxicity to a specific target area. For a more detailed description of photodynamic therapy, see U.S. Pat. Nos. 5,563,262, 5,693,632, 5,354,858, 4,877,872, and 4,988,808, the disclosures of which are incorporated herein by reference.

Phorbines, pheophorbides, and derivatives of chlorophylls are a known class of photoselective compounds useful for photodynamic therapy. See, for example, U.S. Pat. Nos. 4,675,338, 4,656,186, 5,198,460, and 5,506,255. A particularly useful compound that acts as a template for further chemical modifications is the chlorin derivative known as methyl pyropheophorbide. This compound is generally produced by the following reaction scheme:

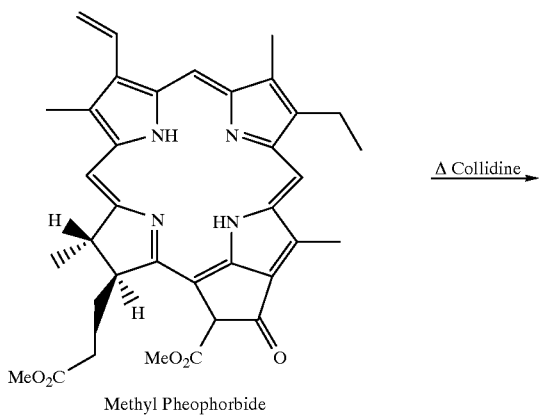

Methyl Pheophorbide

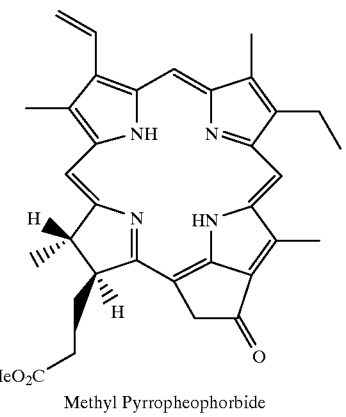

Methyl Pyrropheophorbide

See, U.S. Pat. No. 5,198,460.

The present inventors have found, however, that the demethoxycarbonylation step (depending on the scale of the reaction) is inconsistent in yield and in time to reaction completion. In general, the longer the reaction time, the more decomposition products are produced, which detrimentally impacts the purity and yield of the desired product. It has been found by the present inventors that, in commercial scale production, commercially available 2,4,6-collidine (2,4,6-trimethylpyridine) alone is inadequate in effecting the demethoxycarbonylation reaction, causing major decomposition of the starting pheophorbide due to much longer reflux reaction times.

Accordingly, there is a need for a method for the demethoxycarbonylation of pheophorbides that provides a consistent yield of the desired pyropheophorbide compound.

There is also a need for a method for the demethoxycarbonylation of pheophorbides that provides a reduced reaction time to completion.

There is a further need for a method for the demethoxycarbonylation of pheophorbides that provides the desired pyropheophorbide compound in improved purity.

There is a further need for a method for the demethoxycarbonylation of porphyrins on a large scale that improves the yield, lowers the reaction time, and improves the purity of the desired porphyrin compounds.

SUMMARY OF THE INVENTION

To achieve the advantages and in accordance with the purpose of the invention, as embodied and broadly described herein, a method is provided for the demethoxycarbonylation of porphyrinic compounds. The invention is based on the surprising discovery by the inventors that the presence and amount of water is a rate determining factor in the demethoxycarbonylation reaction of porphyrins such as pheophorbides, which was heretofore not recognized in the art. The method involves reacting under sufficient conditions a porphyrinic compound of the formula I:

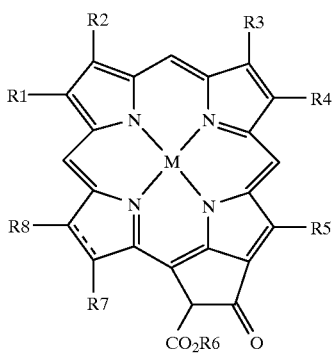

I with a high boiling point solvent to which water has been added. Water can be added in an amount ranging from about 1 to about 300, more particularly 1 to about 200, preferably about 1 to about 100, more preferably about 1 to about 50, and most preferably about 1 to about 16, molar equivalents of water to the starting porphyrinic compound. The reaction is allowed to proceed for a time sufficient to produce a porphyrinic compound of the formula II:

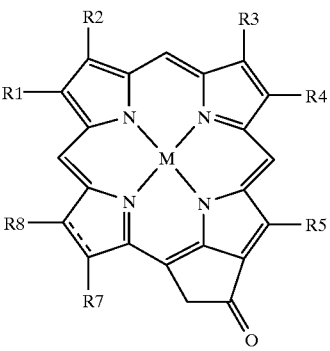

II

In formulae I and II:
$R^1$–$R^8$ can be the same or different and are selected from: hydrogen, halide, alkyl, vinyl, functionalized alkyl, cyclic alkyl (1–6 carbons), substituted or unsubstituted aryl, substituted or unsubstituted alkenyl, substituted or unsubstituted alkynyl, amide, ester, $CH=CHCH_2N(CH_3)_2$, $CH=CHCH_2N^+(CH_3)_3X^-$ (where X is a charge balancing ion), $CX_2CX_3$ (where X is a halogen), $NR^9R^9$, CN, OH, $OR^9$, CHO, $(CH_2)_nOH$, $(CH_2)_nSH$, $(CH_2)_nO$-alkoxy, $CH(OH)CH_3$, $CH(OR^9)CH_3$, $(CH_2)_nSR^9$, $(CH_2)_nOR^9$ (where n=1, 2, 3, or 4, and $R^9$ is a functional group less than or equal to 100,000 daltons); $(CH_2)_nCO_2R^{10}$ (where $R^{10}$ is hydrogen, a physiologically acceptable salt, alkyl (1–6 carbons), substituted or unsubstituted aryl, substituted or unsubstituted alkenyl, or alkyne, and n=1, 2, 3, or 4); $(CH_2)_nCONHR^9$, $(CH_2)_nCON(R^9)_2$, $CO_2R^9$, $CONHR^9$, $CONR^9R^9$, $SR^9$ (where $R^9$ is a functional group less than or equal to 100,000 daltons); $SO_3R^9$, $SO_2NHR^9$, $SO_2N(R^9)_2$, $SO_2N(R^9)_2$, $SO_2N(R^9)_3{}^+X^-$ (where $R^9$ is a functional group less than or equal to 100,000 daltons and X is a charge balancing ion);
M can be $H_2$, Ag, Al, Ce, Co, Cr, Cu, Dy, Er, Fe, Ga, Hf, Ho, In, La, Lu, Mo, Mg, Nd, Pb, Pd, Pr, Pt, Rh, Sb, Sc, Sm, Tb, Th, Ti, Tm, U, V, Y, Tb, Zn, or Zr; and
the bond between $R^7$ and $R^8$ is either a single bond (forming a chlorin) or a double bond (forming a porphyrin).

Preferably, M is $H_2$. $R^1$, $R^3$, $R^5$, $R^6$, and $R^8$ are methyl; $R^2$ and $R^4$ are ethyl; and $R^7$ is —$CH_2CH_2CO_2CH_3$.

In accordance with another embodiment of the invention, as embodied and broadly described herein, a method is provided for the demethoxycarbonylation of pheophorbides by reacting under sufficient conditions a pheophorbide compound of the formula III:

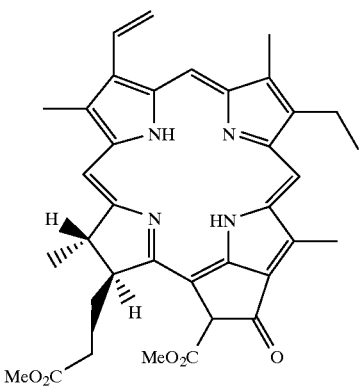

III with a high boiling point solvent to which water has been added. Water can be added in an amount ranging from about 1 to about 300, more particularly about 1 to about 200, preferably about 1 to about 100, more preferably about 1 to about 50, and most preferably about 1 to about 16, molar equivalents of water to the starting pheophorbide compound. The reaction is allowed to proceed for a time sufficient to produce a pyropheophorbide compound of the formula IV:

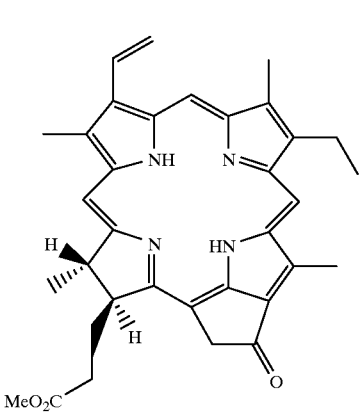

IV

Additional advantages of the invention will be set forth in the detailed description which follows, and in part will be obvious from the description, or may be learned by practice of the invention. The advantages of the invention can be realized and attained by means of the elements and combinations particularly pointed out in the appended claims.

BRIEF DESCRIPTION OF THE DRAWINGS

FIG. 1 is a graph showing the demethoxycarbonylation reaction of methyl pheophorbide (100 mg) in 2,4,6-collidine and 2 equivalents of added water.

FIG. 2 is a graph showing the demethoxycarbonylation reaction of methyl pheophorbide (100 mg) in DMF and 2 equivalents of added water.

FIG. 3 is a graph showing the demethoxycarbonylation reaction of methyl pheophorbide (100 mg) in DMF and 16 equivalents of added water.

FIG. 4 is a graph showing the demethoxycarbonylation reaction of methyl pheophorbide (100 mg) in DMF and 6 equivalents of added water and 1 equivalent of NaCl.

FIG. 5 is a graph showing the demethoxycarbonylation reaction of methyl pheophorbide (100 mg) in toluene 2 equivalents of added water.

FIG. 6 is a graph showing the demethoxycarbonylation reaction of methyl. pheophorbide (100 mg) in sec-butybenzene and 4 equivalents of added water.

FIG. 7 is a graph showing the demethoxycarbonylation reaction of methyl pheophorbide (100 mg) in sec-butybenzene and 16 equivalents of added water.

FIG. 8 is a graph showing the demethoxycarbonylation reaction of methyl pheophorbide (100 mg) in iodobenzene and 16 equivalents of added water.

FIG. 9 is a graph showing the demethoxycarbonylation reaction of methyl pheophorbide (100 mg) in 1-nitropropane and 16 equivalents of added water.

FIG. 10 is a graph showing the demethoxycarbonylation reaction of methyl pheophorbide (100 mg) in pyridine and 16 equivalents of added water.

FIG. 11 is a graph showing the demethoxycarbonylation reaction of methyl pheophorbide (100 mg) in 2,6-lutidine and 16 equivalents of added water.

FIG. 12 is a graph showing the demethoxycarbonylation reaction of methyl pheophorbide (25 g) in pyridine and 13 equivalents of added water.

FIG. 13 is a graph showing the demethoxycarbonylation reaction of methyl pheophorbide (100 mg) in pyridine and 327 equivalents of added water.

FIG. 14 is a graph showing the demethoxycarbonylation reaction of methyl pheophorbide (25 g) in 2,6-lutidine and 13 equivalents of added water.

FIG. 15 is a graph showing the demethoxycarbonylation reaction of methyl pheophorbide (100 mg) in 2-picoline and 16 equivalents of added water.

FIG. 16 is a graph showing the demethoxycarbonylation reaction of methyl pheophorbide (100 g) in 2,6-lutidine and 13 equivalents of added water.

FIG. 17 is a graph showing the demethoxycarbonylation reaction of methyl pheophorbide (100 mg) in distilled 2,4,6-collidine and 327 equivalents of added water.

FIG. 18 is a graph showing the demethoxycarbonylation reaction of methyl pheophorbide (100 mg) in distilled 2,4,6-collidine without added water.

FIG. 19 is a graph showing the demethoxycarbonylation reaction of methyl pheophorbide (100 mg) in various pyridine derivatives and added water.

FIG. 20 is a graph showing the demethoxycarbonylation reaction of methyl pheophorbide (100 mg) in various DMF/water conditions.

FIG. 21 is a graph showing the demethoxycarbonylation reaction of methyl pheophorbide (100 mg) in various benzene derivatives and added water.

FIG. 22 is a graph showing the demethoxycarbonylation reaction of methyl pheophorbide (100 mg and 25 g) in pyridine and added water.

FIG. 23 is a graph showing the demethoxycarbonylation reaction of methyl pheophorbide (100 mg, 25 g, and 100 g) in 2,6-lutidine and added water.

FIG. 24 is a graph showing the demethoxycarbonylation reaction of methyl pheophorbide (2 g) in 2,4,6-collidine with no added water.

FIG. 25 is a graph showing the demethoxycarbonylation reaction of methyl pheophorbide (2 g) in 2,6-lutidine with no added water.

FIG. 26 is a graph showing the demethoxycarbonylation reaction of methyl pheophorbide (2 g) in 2-picoline with no added water.

FIG. 27 is a graph showing the demethoxycarbonylation reaction of methyl pheophorbide (2 g) in pyridine with no added water.

FIG. 28 is a graph showing the demethoxycarbonylation reaction of methyl pheophorbide (2 g) in 2,6-lutidine and 13 equivalents of added water.

FIG. 29 is a graph showing the demethoxycarbonylation reaction of methyl pheophorbide (2 g) in 2-picoline and 13 equivalents of added water.

FIG. 30 is a graph showing the demethoxycarbonylation reaction of methyl pheophorbide (2 g) in 2,4,6-collidine and 13 equivalents of added water.

FIG. 31 is a graph showing the demethoxycarbonylation reaction of methyl pheophorbide (2 g) in pyridine and 13 equivalents of added water.

FIG. 32 is a graph showing the demethoxycarbonylation reaction of methyl pheophorbide (2 g) in 2,4,6-collidine with 13 equivalents of added water and without added water.

FIG. 33 is a graph showing the demethoxycarbonylation reaction of methyl pheophorbide (2 g) in 2,6-lutidine with 13 equivalents of added water and without added water.

FIG. 34 is a graph showing the demethoxycarbonylation reaction of methyl pheophorbide (2 g) in 2-picoline with 13 equivalents of added water and without added water.

FIG. 35 is a graph showing the demethoxycarbonylation reaction of methyl pheophorbide (2 g) in pyridine with 13 equivalents of added water and without added water.

DETAILED DESCRIPTION OF THE PREFERRED EMBODIMENTS

The present inventors have discovered a method for demethoxycarbonylation of porphyrinic molecules like pheophorbides that gives consistent yields and reaction times in a variety of high boiling point solvents in large scale reactions. Critical to the reaction time and resulting purity of the product is the amount of water in the high boiling point solvent. At concentrations of added water ranging from about 1 to about 16 molar equivalents of water to starting pheophorbide (depending on the solvent), the demethoxycarbonylation reaction proceeds rapidly. As concentrations of added water increase above 16 molar equivalents of water to starting pheophorbide, the demethoxycarbonylation reaction kinetics tend to be less favorable. At much higher water concentrations, on the order of around 300 molar equivalents and greater of water to starting pheophorbide, the reaction proceeds more slowly. Thus, surprisingly, the rate of the demethoxycarbonylation reaction is dependent on the amount of water present in the high boiling point solvent.

This discovery is critical to the large scale manufacturing of methyl pyropheophorbide for the following reasons. First, commercially available high boiling point solvents, such as 2,4,6-collidine, will typically have a small percentage of water that enables small scale demethoxycarbonylation reactions (100 s of mgs.) to proceed. This has been shown not to be the case with larger, gram scale reactions. In larger scale industrial processes, the ratio of water in the commercially available solvent to starting pheophorbide will be significantly lower due to loading. This results in longer reaction times and lower yields due to decomposition in the larger scale demethoxycarbonylation reactions.

Moreover, because the rate of reaction is dependent on water, it would be impossible to predict the rate of the reaction unless the amount of water in the commercially available solvent is known accurately. If known, one would need to necessarily compensate for reaction speed by increasing the volume of solvent used. This would make the manufacturing process more expensive compared to separately introducing the water into the process.

As used herein, the term "high boiling point solvent" refers to solvents having a boiling point ranging from about 100 C. to about 2,000 C. The high boiling point solvents that can be used in the method of the invention include, for example, collidines, such as 2,4,6-collidine, 2,3,5-collidine, 2,3,4-collidine, 2,4,5-collidine, 3,4,5-collidine, and 2,3,6-collidine; lutidines, such as 2,3-lutidine, 2,4-lutidine, 2,5-lutidine, 3,4-lutidine, 3,5-lutidine, 2,6-lutidine, and 3,6-lutidine; picolines, such as 2-picoline, 3-picoline, and 4-picoline; N,N-dimethylformamide (DMF); dimethylsulfoxide; pyridine; xylenes; and functionalized benzenes, such as sec-butylbenzene, iodobenzene, and halogenated benzenes. As mentioned, the advantageous ratio of water to methyl pheophorbide varies depending on the particular solvent used.

The following examples are illustrative only and not intended to limit the invention

EXAMPLE 1

Demethoxycarbonylation of methyl pheophorbide-a (100 mg) in 2,4,6-collidine/water (2 equiv.)

To a solution of methyl pheophorbide-a (100 mg, 0.17 mmol) in 2,4,6-collidine (25 mL, distilled) was added distilled water (6 μL, 0.33 mmol, 2 equiv.) and the mixture was refluxed under argon with stirring. The reaction was monitored by HPLC (hexaneacetone, 90:10-mobile phase, LiChrospherCN-column, detection at 425 and 410 nm). After 10 min the reaction was shown to have reached 100% completion by HPLC peak area. The solution was cooled to room temperature after 30 min of reflux and solvent removed under reduced pressure. The residue was precipitated from methylene chloride-methanol to give methyl pyropheophorbide-a (80 mg, 89%).

EXAMPLE 2

Demethoxycarbonylation of methyl pheophorbide-a (100 mg) in DMF/water (2 equiv.)

To a solution of methyl pheophorbide-a (100 mg, 0.17 mmol) in DMF (25 mL) was added distilled water (6 μL, 0.33 mmol, 2 equiv.) and the mixture was refluxed under argon with stirring. The reaction was monitored by HPLC (hexane-acetone, 90:10-mobile phase, LiChrospherCN-column, detection at 425 and 410 nm). After 90 min the reaction was shown to have reached 99.5% completion by HPLC peak area. The solution was cooled to room temperature after 110 min of reflux and solvent removed under reduced pressure. The residue was precipitated from methylene chloride-methanol to give methyl pyropheophorbide-a (80 mg, 89%).

EXAMPLE 3

Demethoxycarbonylation of methyl pheophorbide-a (100 mg) in DMF/water (16 equiv.)

To a solution of methyl pheophorbide-a (100 mg, 0.17 mmol) in DMF (25 mL) was added distilled water (48 μL, 2.7 mmol, 16 equiv.) and the mixture was refluxed under argon with stirring. The reaction was monitored by HPLC (hexane-acetone, 90:10-mobile phase, LiChrospherCN-column, detection at 425 and 410 nm). After 60 min the reaction was shown to have reached 99.6% completion by HPLC peak area. The solution was cooled to room temperature after 100 min of reflux and solvent removed under reduced pressure. The residue was precipitated from methylene chloride-methanol to give methyl pyropheophorbide-a (50 mg, 56%).

EXAMPLE 4

Demethoxycarbonylation of methyl pheophorbide-a (100 mg) in DMF/water (6 equiv.)/NaCl (1 equiv.)

To a solution of methyl pheophorbide-a (100 mg, 0.17 mmol) in DMF (15 mL) was added distilled water (18 L, 1.0 mmol, 6 equiv.) and NaCl (10 mg, 0.18 mmol, 1 equiv.). The mixture was refluxed under argon with stirring. The reaction was monitored by HPLC (hexane-acetone, 90:10-mobile phase, LiChrospherCN-column, detection at 425 and 410 nm). After 40 min the reaction was shown to have reached 99.6% completion by HPLC peak area and a faint baseline spot on TLC (5% acetone/methylene chloride). The solution was cooled to room temperature after 60 min of reflux and solvent removed under reduced pressure. The residue was precipitated from methylene chloride-methanol to give methyl pyropheophorbide-a (60 mg, 67%).

EXAMPLE 5

Demethoxycarbonylation of methyl pheophorbide-a (100 mg) in toluene/water (2 equiv.)

To a solution of methyl pheophorbide-a (100 mg, 0.17 mmol) in toluene (25 mL) was added distilled water (6 μL, 0.33 mmol, 2 equiv.) and the mixture was refluxed under argon with stirring. The reaction was monitored by HPLC (hexane-acetone, 90:10-mobile phase, LiChrospherCN-column, detection at 425 and 410 nm). After 60 min the reaction was shown to have yielded only trace amounts of desired product by HPLC. After 80 min of reflux, more distilled water (48 μL, 2.7 mmol, 16 equiv.) was added and reflux continued. Again the reaction was monitored by HPLC. The HPLC of reaction aliquot after 10 min and 30 min showed no significant change. The reaction was discontinued.

EXAMPLE 6

Demethoxycarbonylation of methyl pheophorbide-a (100 mg) in sec-butylbenzene/water (4 equiv.)

To a solution of methyl pheophorbide-a (100 mg, 0.17 mmol) in sec-butylbenzene (25 mL) was added distilled water (12 μL, 0.67 mmol, 4 equiv.) and the mixture was refluxed under argon with stirring. The reaction was monitored by HPLC (hexaneacetone, 90:10-mobile phase, LiChrospherCN-column, detection at 425 and 410 nm). The HPLC of reaction aliquot after 30 min, 60 min, 90 min and 110 min showed slow increase of product percentage. At 110 min, 30% of the starting methyl pheophorbide-a remained (by HPLC peak area) and TLC (5% acetone/methylene chloride) showed a baseline spot. The reaction was stopped, cooled to room temperature and solvent removed under reduced pressure. The crude product was not purified.

EXAMPLE 7

Demethoxycarbonylation of methyl pheophorbide-a (100 mg) in sec-butylbenzene/water (16 equiv.)

To a solution of methyl pheophorbide-a (100 mg, 0.17 mmol) in sec-butylbenzene (25 mL) was added distilled water (48 µL, 2.7 mmol, 16 equiv.) and the mixture was refluxed under argon with stirring. The reaction was monitored by HPLC (hexaneacetone, 90:10-mobile phase, LiChrospherCN-column, detection at 425 and 410 nm). The HPLC of the reaction aliquots after 30 min, 60 min and 90 min showed a slow increase of product percentage. At 90 min, 50% of the starting methyl pheophorbide-a remained (by HPLC peak area) and TLC (5% acetone/methylene chloride) showed a heavy baseline spot. The reaction was stopped, cooled to room temperature and solvent removed under reduced pressure. The crude product was not purified.

EXAMPLE 8

Demethoxycarbonylation of methyl pheophorbide-a (100 mg) in iodobenzene/water (16 equiv.)

To a solution of methyl pheophorbide-a (100 mg, 0.17 mmol) in iodobenzene (25 mL) was added distilled water (48 µL, 2.7 mmol, 16 equiv.) and the mixture was refluxed under argon with stirring. The reaction was monitored by HPLC (hexane-acetone, 90:10-mobile phase, LiChrospherCN-column, detection at 425 and 410 nm). The HPLC of the reaction aliquots after 30 min, 60 min, 90 min and 110 min showed a slow increase of product. At 110 min, 50% of the starting methyl pheophorbide-a remained (by HPLC peak area) and TLC (5% acetone/methylene chloride) showed a baseline spot. The reaction was stopped, cooled to room temperature and solvent removed under reduced pressure. The crude product was not purified.

EXAMPLE 9

Demethoxycarbonylation of methyl pheophorbide-a (100 mg) in 1-nitropropane/water (16 equiv.)

To a solution of methyl pheophorbide-a (100 mg, 0.17 mmol) in 1-nitropropane (25 mL) was added distilled water (48 µL, 2.7 mmol, 16 equiv.) and the mixture was refluxed under argon with stirring. The reaction was monitored by HPLC (hexane-acetone, 90:10-mobile phase, LiChrospherCN-column, detection at 425 and 410 nm). The HPLC of reaction aliquot after 30 min showed only 9% formation of the product. The reaction was stopped.

EXAMPLE 10

Demethoxycarbonylation of methyl pheophorbide-a (100 mg) in pyridine/water (16 equiv.)

To a solution of methyl pheophorbide-a (100 mg, 0.17 mmol) in pyridine (25 mL) was added distilled water (48 µL, 2.7 mmol, 16 equiv.) and the mixture was refluxed under argon with stirring. The reaction was monitored by HPLC (hexane-acetone, 90:10-mobile phase, LiChrospherCN-column, detection at 425 and 410 nm). The HPLC of the reaction aliquots after 2 h and 20 min showed 87% completion (by peak area). After 2 h and 40 min of reflux, more distilled water (32 L, 1.8 mmol, 11 equiv.) was added and reflux continued. An HPLC of reaction aliquot at 5 h and 40 min showed 99.5% completion (by peak area). The solution was cooled to room temperature and solvent removed under reduced pressure. The residue was crystallized from methylene chloride-methanol to give methyl pyropheophorbide-a (50 mg, 56%).

EXAMPLE 11

Demethoxycarbonylation of methyl pheophorbide-a (100 mg) in 2,6-lutidine/water (16 equiv.)

To a solution of methyl pheophorbide-a (100 mg, 0.17 mmol) in 2,6-lutidine (25 mL) was added distilled water (48 µL, 2.7 mmol, 16 equiv.) and the mixture was refluxed under argon with stirring. The reaction was monitored by HPLC (hexane-acetone, 90:10-mobile phase, LiChrospherCN-column, detection at 425 and 410 nm). The HPLC of reaction aliquot after 30 min showed 100% completion (by peak area). The solution was cooled to room temperature and solvent removed under reduced pressure. The residue was crystallized from methylene chloride-methanol to give methyl pyropheophorbide-a (78 mg, 87%).

EXAMPLE 12

Demethoxycarbonylation of 25 g of methyl pheophorbide-a in pyridine/water (13 equiv.)

To a solution of methyl pheophorbide-a (25 g, 42.5 mmol) in pyridine (1 L) was added distilled water (10 mL, 556 mmol, 13 equiv., 1% v/v) and the mixture was refluxed under argon with stirring. The reaction was monitored by HPLC (hexane-acetone, 90:10-mobile phase, LiChrospherCN-column, detection at 425 and 410 nm). An HPLC of the reaction aliquot after 9 hours of reflux showed 99% completion (by peak area). The solution was cooled to room temperature after 10 hours of reflux and solvent removed under reduced pressure. The residue was precipitated first from methylene chloride-hexane and then methylene chloride/methanol. The solid collected was then purified on a silica gel column, eluted with 2% acetone/methylene chloride. The desired fraction was collected and precipitated from methylene chloride/methanol to give methyl pyropheophorbide-a (20.3 g, 91%).

EXAMPLE 13

Demethoxycarbonylation of methyl pheophorbide-a (100 mg) in pyridine/water (327 equiv.)

To a solution of methyl pheophorbide-a (100 mg, 0.17 mmol) in pyridine (25 mL) was added distilled water (1 mL, 56 mmol, 327 equiv., 4% v/v) and the mixture was refluxed under argon with stirring. The reaction was monitored by HPLC (hexane-acetone, 90:10-mobile phase, LiChrospherCN-column, detection at 425 and 410 nm). HPLCs of reaction aliquots after 30 min, 60 min, 90 min and 120 min showed a slow increase of desired product. At 220 min, 43% of the starting methyl pheophorbide-a remained (by HPLC peak area). The reaction was stopped, cooled to room temperature and solvent removed under reduced pressure. The crude product was not purified.

EXAMPLE 14

Demethoxycarbonylation of 25 g of methyl pheophorbide-a in 2,6-lutidine/water (13 equiv.)

To a solution of methyl pheophorbide-a (25 g, 42.5 mmol) in 2,6-lutidine (1 L) was added distilled water (10 mL, 556 mmol, 13 equiv., 1% v/v) and the mixture was refluxed under argon with stirring. The reaction was monitored by HPLC (hexane-acetone, 90:10-mobile phase, LiChrospherCN-column, detection at 425 and 410 nm). After 100 min. of reflux, the HPLC of reaction aliquots showed 99.7% of completion. The solution was cooled to room temperature after 120 min of reflux and solvent removed under reduced pressure. Hexane (100 mL) was added and the solid was collected by filtration and rinsed with hexane to remove any traces of 2,6-lutidine. The solid was then precipitated from methylene chloride-methanol to give methyl pyropheophorbide-a (20.3 g, 91%).

EXAMPLE 15

Demethoxycarbonylation of methyl pheophorbide-a (100 mg) in 2-picoline/water (16 equiv.)

To a solution of methyl pheophorbide-a (100 mg, 0.17 mmol) in 2-picoline (25 mL) was added distilled water (48 μL, 2.7 mmol, 16 equiv.) and the mixture was refluxed under argon with stirring. The reaction was monitored by HPLC (hexane-acetone, 90:10-mobile phase, LiChrospherCN-column, detection at 425 and 410 nm). The HPLC of reaction aliquot after 120 min showed 99.4% of completion (by peak area) and TLC (5% acetone/methylene chloride) showed a heavy baseline. The solution was cooled to room temperature and solvent removed under reduced pressure. The crude product was not purified.

EXAMPLE 16

Demethoxycarbonylation of 100 g of methyl pheophorbide-a in 2,6-lutidine/water (13 equiv.)

To a solution of methyl pheophorbide-a (100 g, 165 mmol) in 2,6-lutidine (4 L) was added distilled water (40 mL, 2.22 mol, 13 equiv., 1% v/v) and the mixture was refluxed under argon with stirring. The reaction was monitored by HPLC (hexane-acetone, 90:10-mobile phase, LiChrospherCN-column, detection at 425 and 410 nm). The HPLC of reaction aliquot after 90 min showed 99.5% of completion. The solution was cooled to room temperature after 120 min of reflux and solvent removed under reduced pressure with water bath at 45–50° C. Hexane (120 mL) was added and the solid was collected by filtration and rinsed with hexane to remove any traces of 2,6-lutidine. The solid was vacuum dried to give methyl pyropheophorbide-a (89.6 g, 99%).

EXAMPLE 17

Demethoxycarbonylation of methyl pheophorbide-a (100 mg) in distilled 2,4,6-collidine/water (327 equiv.)

To a solution of methyl pheophorbide-a (100 mg, 0.17 mmol) in 2,4,6-collidine (25 mL, distilled) was added distilled water (1 mL, 56 mmol, 327 equiv., 4% v/v) and the mixture was refluxed under argon with stirring. The reaction was monitored by HPLC (hexane-acetone, 90:10-mobile phase, LiChrospherCN-column, detection at 425 and 410 nm). After 90 min, the reaction was shown to have reached 99.5% completion by HPLC peak area. The solution was cooled to room temperature and solvent removed under reduced pressure. Hexane (10 mL) was added and the precipitated porphyrin was collected by filtration and rinsed with hexane to give methyl pyropheophorbide-a (65 mg, 72%).

EXAMPLE 18

Demethoxycarbonylation of methyl pheophorbide-a (100 mg) in distilled 2,4,6-collidine Methyl pheophorbide-a (100 mg, 0.17 mmol) was added to 2,4,6-collidine (25 mL, distilled) and the mixture was refluxed under argon with stirring. The reaction was monitored by HPLC (hexane-acetone, 90:10-mobile phase, LiChrospherCN-column, detection at 425 and 410 nm). After 20 min, the reaction was shown to have reached 100% completion by HPLC peak area. The solution was cooled to room temperature and solvent removed under reduced pressure. Hexane (10 mL) was added to the flask and the precipitated residue collected by filtration and rinsed with hexane to give methyl pyropheophorbide-a (70 mg, 77%).

EXAMPLE 19

Demethoxycarbonylation of methyl pheophorbide-a (100 mg) in distilled 2,4,6-collidine/water (16 equiv.)

To a solution of methyl pheophorbide-a (100 mg, 0.17 mmol) in 2,4,6-collidine (25 mL, distilled) was added distilled water (48 μL, 2.7 mmol, 16 equiv.) and the mixture was refluxed under argon with stirring. The reaction was monitored by HPLC (hexaneacetone, 90:10-mobile phase, LiChrospherCN-column, detection at 425 and 410 nm). After 10 min, the reaction was shown to have reached 100% completion by HPLC peak area. The solution was cooled to room temperature and solvent removed under reduced pressure. Hexane (10 mL) was added to the flask and the precipitated residue collected by filtration and rinsed with hexane to give methyl pyropheophorbide-a (70 mg, 77%).

EXAMPLE 20

Demethoxycarbonylation of methyl pheophorbide-a (100 mg) in commercial available 2,4,6-collidine Methyl pheophorbide-a (100 mg, 0.17 mmol) was added to commercially available 2,4,6-collidine (25 mL, Aldrich) and the mixture was refluxed under argon with stirring. The reaction was monitored by HPLC (hexane-acetone, 90:10-mobile phase, LiChrospherCN-column, detection at 425 and 410 nm). After 10 min, the reaction was shown to have reached 100% completion by HPLC peak area. The solution was cooled to room temperature and solvent removed under reduced pressure. Hexane (10 mL) was added to the flask and the precipitated residue collected by filtration and rinsed with hexane to give methyl pyropheophorbide-a (71 mg, 78%).

EXAMPLE 21

Larger scale demethoxycarbonylation of methyl pheophorbide-a (15.8 g) in 2,4,6-collidine a) Methyl pheophorbide-a (15.8 g, 26.0 mmol) was added to commercially available 2,4,6-collidine (1.5 L, Aldrich), and the mixture was heated to reflux with stirring. After 30 hours of reflux, the reaction was still incomplete by TLC and HPLC and a heavy baseline was observed. The solution was cooled to room temperature and solvent removed under reduced pressure. The residue was first precipitated twice from methylene chloride/methanol, then purified on a silica gel column with 10% ethyl acetate/methylene chloride. TLC of the desired fraction showed presence of methyl pheophorbide and a heavy baseline. After evaporating off the solvent, the residue was dissolved in 2,4,6-collidine (500 mL) and heated to reflux again. After 2 days of reflux, TLC of the reaction solution still showed the presence of methyl pheophorbide. The reaction solution was evaporated to dryness and the residue was purified on a silica gel column. The desired fraction was evaporated to dryness and the residue was redissolved in methylene chloride, precipitated twice with methanol, and finally purified on a silica gel flash column to give 3.4 g of methyl pyropheophorbide-a.

b) Methyl pheophorbide-a (23 g, 37.9 mmol) was added to distilled 2,4,6-collidine (700 mL, Aldrich) and the mixture was refluxed under argon with stirring. After 7 hours of reflux, TLC showed the majority of methyl pheophorbide-a remained. Distilled water (2.5 mL, 139 mmol, 3.7 equiv.) was added and the solution was continued to reflux under argon. After 45 min. the reaction was complete by TLC. The solution was cooled to room temperature and solvent removed under reduced pressure. The residue was precipitated from methylene chloride/methanol, then purified on a silica gel column. The desired fraction was collected, solvent was evaporated off, and the fraction was precipitated from methylene chloride/methanol to give methyl pyropheophorbide-a (17 g, 81%).

EXAMPLE 22

Demethoxycarbonylation of methyl pheophorbide-a (2 g) in 2,4,6-collidine

A 250 mL round-bottom flask, Friedrichs condenser, magnetic stirring bar, and gas adapter were preheated 24 hrs in a drying oven (100° C.). The glassware was assembled and left under argon using a gas bubbler. Methyl pheophorbide (2 g, 8000516-112-1) and 2,4,6-collidine (80 mL, 02201BQ/freshly opened/Aldrich) were charged to the round-bottom flask. With a heating mantle and a magnetic stirrer, the solution was heated and stirred. Reaction was monitored by HPLC (Beckman/System Gold/Hexane-Acetone, 90:10-mobile phase, LiChrospher CN-column, detection at 410 nm). Aliquots were taken out every 10 minutes for the first 2 hours. Aliquots were taken out every half-hour for the next two hours. The solution was allowed to reflux overnight. After 16 hrs of reflux, HPLC of the reaction aliquot showed incomplete reaction. TLC showed significant baseline impurities. 2,4,6-collidine was rotoevaporated off (90° C.). Several attempts to re-crystallize product in MeOH/$CH_2Cl_2$ and Hexane/$CH_2Cl_2$ failed probably due to impurities.

EXAMPLE 23

Demethoxycarbonylation of methyl pheophorbide-a (2 g) in pyridine

A 3-neck 250 mL round-bottom flask, Friedrichs condenser, magnetic stirring bar, 2 stoppers and gas adapter were preheated 24 hrs in a drying oven (100° C.). The glassware was assembled and left under argon using a gas bubbler. Methyl pheophorbide (2 g, 8000516-112-1) and pyridine (80 mL, TR08119LR/freshly opened/Aldrich) were charged to the round-bottom flask. With a heating mantle and a magnetic stirrer, the solution was heated and stirred. The reaction was monitored by HPLC (Beckman/System Gold/Hexane-Acetone, 90:10-mobile phase, LiChrospher CN-column, detection at 410 nm). Aliquots were taken out every 10 minutes for the first 2 hours. Aliquots were taken out every half-hour for the next 4 hours. The reaction was allowed to reflux overnight. The following morning, the reaction was monitored every half-hour for 7 hours. The solution was allowed to reflux overnight. The next morning, the reaction was monitored intermittently. After 53 hrs of reflux, HPLC of reaction aliquot showed incomplete reaction. TLC showed significant baseline impurities.

EXAMPLE 24

Demethoxycarbonylation of methyl pheophorbide-a (2 g) in 2,6-lutidine

A 3-neck 250 mL round-bottom flask, Friedrichs condenser, magnetic stirring bar, 2 stoppers and gas adapter were preheated 24 hrs in a drying oven (100° C.). The glassware was assembled and left under argon using a gas bubbler. Methyl pheophorbide (2 g, 8000516-112-1) and 2,6-lutidine (80 mL, A010596301/freshly opened/Acros) were charged to the round-bottom flask. With a heating mantle and magnetic stirrer, the solution was heated and stirred. Reaction was monitored by HPLC (Beckman/System Gold/Hexane-Acetone, 90:10-mobile phase, LiChrospher CN-column, detection at 410 nm). Aliquots were taken out every 10 minutes for the first 2 hours. Aliquots were taken out every half-hour for the next 2 hours. The reaction was allowed to reflux overnight. The next morning, the reaction was monitored intermittently for 7 hours. After 27 hrs of reflux, HPLC of the reaction aliquot showed incomplete reaction. TLC showed some baseline impurities.

EXAMPLE 25

Demethoxycarbonylation of methyl pheophorbide-a (2 g) in 2-picoline

A one-neck 250 mL round-bottom flask, Friedrichs condenser, magnetic stirring bar, and gas adapter were preheated 24 hrs in a drying oven (100° C.). The glassware was assembled and left under argon using a gas bubbler. Methyl pheophorbide (2 g, 8000516-112-1) and 2-picoline (80 mL, 12320PY/Aldrich) were charged to the round-bottom flask. With a heating mantle and magnetic stirrer, the solution was heated and stirred. Reaction was monitored by HPLC (Beckman/System Gold/Hexane-Acetone, 90:10-mobile phase, LiChrospher CN-column, detection at 410 nm). Aliquots were taken out every 10 minutes for the first 3 hours. Aliquots were taken out every half-hour for the following 1 hour. Reaction was cooled and left overnight in the dark. The next morning, the reaction was reheated to reflux. Aliquots were taken out every half-hour for the next 5 hours. After 9 hrs of reflux, the reaction was nearly complete by HPLC. HPLC showed 10 percent impurities and TLC showed some baseline impurities.

EXAMPLE 26

Demethoxycarbonylation of methyl pheophorbide-a (2 g) in 2,4,6-collidine/water (13 equiv.)

To a solution of methyl pheophorbide-a (2.0 g, 3.3 mmol) in 2,4,6-collidine (80 mL) was added distilled water (0.8 mL) and the mixture was refluxed under argon with stirring. The reaction was monitored by HPLC (Waters instrument, hexane-acetone, 90:10-mobile phase; LiChrospher CN-column; detection at 410 nm). The reaction was continued for 70 min, cooled to room temperature, and solvent removed under reduced pressure. The residue was precipitated from methylene chloride-hexane to give methyl pyropheophorbide (1.6 mg, 89%).

EXAMPLE 27

Demethoxycarbonylation of methyl pheophorbide-a (2 g) in pyridine/water (13 equiv.)

To a solution of methyl pheophorbide-a (2.0 g, 3.3 mmol) in pyridine (80 mL) was added distilled water (0.8 mL) and the mixture was refluxed under argon with stirring. The reaction was monitored by HPLC (Waters instrument, hexane-acetone, 90:10-mobile phase; LiChrospher CN-column; detection at 410 nm). The HPLC of reaction aliquot after 8.5 h of reflux showed <1% (peak area) of starting methyl pheophorbide-a. The reaction was stopped, cooled to room temperature and solvent removed under reduced pressure. The residue was precipitated from methylene chloride-hexane to give methyl pyropheophorbide-a (1.8 g, 100%).

EXAMPLE 28

Demethoxycarbonylation of methyl pheophorbide-a (2 g) in 2,6-lutidine/water (13 equiv.)

To a solution of methyl pheophorbide-a (2.0 g, 3.3 mmol) in 2,6-lutidine (80 mL) was added distilled water (0.8 mL) and the mixture was refluxed under argon with stirring. The reaction was monitored by HPLC (Waters instrument, hexane-acetone, 90:10-mobile phase; LiChrospher CN-column; detection at 410 nm). The reflux was continued for 110 min, cooled to room temperature, and solvent removed under reduced pressure. The residue was precipitated from methylene chloride-hexane to give methyl pyropheophorbide (1.6 g, 89%).

EXAMPLE 29

Demethoxycarbonylation of methyl pheophorbide-a (2 g) in 2-picoline/water (13 equiv.)

To a solution of methyl pheophorbide-a (2.0 g, 3.3 mmol) in 2-picoline (80 mL) was added distilled water (0.8 mL) and the mixture was refluxed under argon with stirring. The reaction was monitored by HPLC (Waters instrument, hexane-acetone, 90:10-mobile phase; LiChrospher CN-column; detection at 410 nm). The reflux was continued for 210 min, cooled to room temperature, and solvent removed under reduced pressure. The residue was precipitated from methylene chloride-hexane to give methyl pyropheophorbide (1.6 g, 89%).

Results and Discussion

A study of the demethoxycarbonylation of methyl pheophorbide was carried out at several scales (100 mg, 2 g, 12 g, 25 g, 100 g) using various solvents and conditions. In order to diversify this study, four types of common organic solvents were selected to study the reaction. They were pyridine derivatives, DMF, benzene derivatives and nitropropane. The results of these studies are discussed below.

A. Demethoxycarbonylation in pyridine type solvents

Demethoxycarbonylation of methylpheophorbide was studied in various pyridine derivatives of different boiling point (pyridine, 2-picoline, 2,6-lutidine and 2,4,6-collidine, at several different scales (100 mg, 2 g, 25 g, 100 g). The 100 mg scale results are summarized in FIGS. 1, 10, 11, 13, 15, 17, 18, 19, 22 and 23. The 2 g scale results are summarized in FIGS. 24, 25, 26, 27, 28, 29, 30, 31, 32, 33, 34 and 35. The 25 g scale reactions are summarized in FIGS. 12, 14, 22 and 23. The 10 g scale results are summarized in FIGS. 16 and 23.

There appeared to be little difference in the rate of demethoxycarbonylation of methyl pheophorbide at the 100 mg scale in "dry" 2,4,6-collidine vs "wet" 2,4,6-collidine (2 equiv. of water). A larger scale demethoxycarbonylation (2 g) was undertaken to show that indeed a significant rate difference occurred when water was introduced in gram scale demethoxycarbonylation reactions.

To further illustrate the fact that the addition of water actually enables large scale manufacturing of methyl pyropheophorbide, reactions were performed up to 100 g scales. The results of the small scale and large scale demethoxycarbonylation reaction shows that the amount of water present in the reaction significantly alters the reaction rate and subsequent yield and purity of the final product. A few equivalents of water were shown to accelerate the reaction, but higher concentrations of water were shown to slow the reaction rate. In general, prolonged reaction time produced more impurities. The experiments also showed that if the ratio of concentrations of methyl pheophorbide to water remained the same, the reaction rates were the same in 25-g scale and 100-g scale. Each pyridine "type" solvent will now be discussed in detail.

1. Pyridine (B.P. 115° C.)

a. 100 mg reaction with water (16 equiv.)

Demethoxycarbonylation of methyl pheophorbide in pyridine containing 16 equivalents of water was performed. HPLC chromatograms showed steady increase of methyl pyropheophorbide to 86.6% over the first 140 minutes. With the intention of increasing reaction, additional water (11 equivalents) was added, but no significant improvement was observed after 30 minutes. The reaction was eventually complete after 5 hours and 40 min. of reflux.

No impurity was observed in HPLC chromatogram of the final reaction aliquot, and a baseline spot was observed on silica gel TLC (5% acetone/methylene chloride). The yield after precipitation from methylene chloride/methanol was 56%. HPLC of the reaction aliquots was run every 30-min. to construct a reaction profile. FIG. 10 shows a plot of percent methyl pyropheophorbide and methyl pheophorbide vs. reaction time.

b. 100 mg reaction with water (327 equiv., 4% v/v)

The rate of the demethoxycarbonylation reaction was slower with 327 equivalents of water (1 mL in 25 mL pyridine) than with 16 equivalents. Methyl pyropheophorbide formation was 57.0% after 3 h. and 40 min. of reflux, compared to 95.5% with 16 equivalents of water. The excess of water probably lowers the boiling point of the reaction solution and subsequently slows the reaction. The HPLC chromatogram showed no impurity in the final reaction aliquot. FIG. 13 shows a plot of percent methyl pyropheophorbide and methyl pheophorbide vs. reaction time.

c. 2 g scale in commercially available pyridine with and without water.

FIG. 27 shows the reaction rate of demethoxycarbonylation in commercially available pyridine. FIG. 31 shows the reaction rate of demethoxycarbonylation in commercially available pyridine with 13 equiv. of water added. FIG. 35 summarizes the two reactions. As can be clearly seen, the addition of water to commercial pyridine increases the rate of the demethoxycarbonylation reaction significantly.

d. Large scale 25 g pyridine reaction with water (13 equiv., 1% v/v)

A demethoxycarbonylation reaction of 25 g of Methyl pheophorbide in pyridine (1 L) and water (10 mL, 13 equiv., 1% v/v) was monitored by HPLC. In this reaction the concentration of methyl pheophorbide in pyridine was 6-fold of that in the 100-mg reaction. The reaction was monitored by HPLC hourly and it was complete after 10 hours reflux. The reaction rate was slower than that in 100-mg scale, which was complete in 6 hours (FIG. 22).

Silica gel TLC of the crude product showed impurities with red color (less polar, probably porphyrins) and green color. Prolonged reaction time produced more impurities and significant baseline impurities were seen on silica gel TLC.

HPLC of the reaction aliquots was run every hour to construct a reaction profile. FIG. 12 shows a plot of percent methyl pyropheophorbide and methyl pheophorbide vs. reaction time.

2. 2-Picoline (B.P. 128–129° C.) with water (16 equiv.)
   a. 100 mg scale with 16 equiv. water 2-Picoline, which has a higher boiling point than pyridine, would be expected to have a faster reaction rate. The demethoxycarbonylation of 100 mg of methylpheophorbide in 2-picoline/water (16 equiv.) was complete in 2 hours. However an unknown peak at a RRT=1.728 (6.3–9.7%) was observed and TLC showed a heavy baseline spot. FIG. 15 shows a plot of percent methyl pyropheophorbide and methyl pheophorbide vs. reaction time.

b. 2 g scale in commercially available 2-picoline with and without water.

FIG. 26 shows the reaction rate of demethoxycarbonylation in commercially available 2-picoline. FIG. 29 shows the reaction rate of demethoxycarbonylation in commercially available 2-picoline with 13 equiv. of water added. FIG. 34 summarizes the two reactions. As can be clearly seen, the addition of water to commercial 2-picoline increases the rate of the demethoxycarbonylation reaction significantly.

3. 2,6-Lutidine (B.P. 143–145° C.)
   a. 100 mg scale with water (16 equiv.)

2,6-Lutidine is a pyridine derivative with a boiling point of 143–145° C. It is inexpensive and commercially available in large quantity. Demethoxycarbonylation of methyl pheophorbide (100 mg) in 2,6-lutidine/water (16 equiv.) was complete in 20 minutes with no impurity observed on HPLC chromatogram. TLC also showed a very minor faint baseline impurity. FIG. 11 shows a plot of percent methyl pyropheophorbide and methyl pheophorbide vs. reaction time.

b. 2 g scale in commercially available 2,6-Lutidine with and without water.

FIG. 25 shows the reaction rate of demethoxycarbonylation in commercially available 2,6-lutidine. FIG. 28 shows the reaction rate of demethoxycarbonylation in commercially available 2,6-lutidine with 13 equiv. of water added. FIG. 33 summarizes the two reactions. As can be clearly seen, the addition of water to commercial 2,6-lutidine increases the rate of the demethoxycarbonylation reaction significantly.

c. Large scale with water (13 equiv., 1% v/v)
      i. 25-g scale

Demethoxycarbonylation of methyl pheophorbide (25 g) in 2,6-lutidine was further investigated to prove efficacy. A reaction of 25 g of methyl pheophorbide in 2,6-lutidine (1 L) and water (10 mL, 13 equiv., 1% v/v) was monitored by HPLC. In this reaction, the concentration of methyl pheophorbide in 2,6-lutidine was 6-fold greater than that in the 100-mg reaction. The reaction was complete after 80 min. of reflux (<1% of methyl pheophorbide) and the product was precipitated from methylene chloride/methanol to give 91% yield.

The reaction rate was, as expected, slower than that in 100-mg scale which completed in 20 minutes (FIG. 23). The HPLC chromatogram showed 99% of methyl pyropheophorbide in the final reaction aliquot and TLC (5% acetone/methylene chloride) showed a very faint baseline spot. FIG. 14 shows a plot of percent methyl pyropheophorbide and methyl pheophorbide vs. reaction time.

ii. 100 g scale

This reaction showed that when the reaction solution had the same concentrations of methyl pheophorbide and water, the reaction rates were the same in any scale (FIG. 23). A reaction of 100 g of methyl pheophorbide in 2,6-lutidine (4 L) and water (40 mL, 13 equiv., 1% v/v) was monitored by HPLC. The reaction was complete after 80 min. of reflux. The HPLC chromatogram showed no impurity in the final reaction aliquot. The isolated yield was quantitative with purity >99%. FIG. 16 shows a plot of percent methyl pyropheophorbide and methyl pheophorbide vs. reaction time.

4. 2,4,6-collidine (B.P. 171–172° C.)

2,4,6-collidine, also called 2,4,6-trimethylpyridine, is a high boiling point solvent. The result showed that the addition of water to the reaction dramatically accelerated the reaction. The effect was not so striking when the reaction was undertaken on a small scale (100 mg), but at larger scales (2 g, 25 g) the reaction rate was improved significantly.

a. 100 mg reaction
      i. Distilled 2,4,6-collidine with water (2 equiv.)

Demethoxycarbonylation in 2,4,6-collidine/water (2 equiv.) was complete after 10 min. of reflux. The HPLC chromatogram showed no impurity in the reaction aliquot (FIG. 1). The product after precipitated from methylene chloride/methanol gave 80% yield.

ii. Distilled 2,4,6-collidine with water (16 equiv.)

The reaction was complete in 10 min. of reflux and the HPLC showed no impurity in the reaction aliquot.

iii. Distilled 2,4,6-collidine with water (327 equiv.)

The reaction was complete after 90 min. of reflux. An impurity at RRT=1.570 was observed at 0.15%. FIG. 17 shows a plot of percent methyl pyropheophorbide and methyl pheophorbide vs. reaction time.

iv. Distilled 2,4,6-collidine without water

The reaction was complete after 20 min. of reflux. Compared to the reaction with water (2 equiv. or 16 equiv.), this reaction is slower (FIG. 18) albeit modestly.

b. 2 g scale in commercially available 2,4,6-collidine with and without water.

FIG. 24 shows the reaction rate of demethoxycarbonylation in commercially available 2,4,6-collidine. FIG. 30 shows the reaction rate of demethoxycarbonylation in commercially available 2,4,6-collidine with 13 equiv. of water added. FIG. 32 summarizes the two reactions. As can be clearly seen the addition of water to commercial 2,4,6-collidine increases the rate of the demethoxycarbonylation reaction significantly. In addition the quality and yield of the methyl pyropheophorbide produced using commercial 2,4,6-collidine is far inferior when compared to the reaction with water added.

c. ~25 g reactions in commercially available 2,4,6-collidine with and without water.

This reaction showed that addition of water is necessary when the reaction scale is performed on scales larger than 100 milligrams. The reaction of 23-g of methyl pheophorbide in 2,4,6-collidine (700 mL) was incomplete after 7 hours of reflux as observed by TLC. The reaction was complete 45 min. after the addition of 2.5 mL of water.

B. Demethoxycarbonylation in various DMF/water conditions (100 mg scale).

The demethoxycarbonylation in DMF was much faster than in pyridine and 2-picoline, but slower than in 2,6-lutidine and 2,4,6-collidine. The results are summarized in FIG. 20.

1. With water (2 equiv.)

Demethoxycarbonylation of methyl pheophorbide in DMF/water (2 equiv.) was monitored by HPLC. The reaction was complete after 80 min. of reflux (<0.5% of Methyl pheophorbide). The product was precipitated from methylene chloride/methanol to give 89% yield. The baseline of HPLC chromatogram showed presence of small quantities of impurities (total, approx. 1%, by peak area), and TLC showed a faint baseline spot (5% acetone/methylene chloride). A plot of percent methyl pyropheophorbide and methyl pheophorbide vs. reaction time is shown in FIG. 2.

2. With water (16 equiv.)

A similar reaction in DMF with 16 equivalents of water provided methyl pyropheophorbide after refluxing for 50 min. (<0.5% of methyl pheophorbide). The product was precipitated from methylene chloride/methanol to give 56% yield. An HPLC chromatogram of the final aliquot showed the presence of small quantities of impurities (1–1.5% by peak area). Compared with the reaction using 2 equivalents of water, the reaction using 16 equivalents of water was slightly faster, but a greater amount of impurities at RRT= 0.83 was observed. A plot of percent methyl pyropheophorbide and methyl pheophorbide vs. reaction time is shown in FIG. 3.

3. With water (6 equiv.) and NaCl (1 equiv.)

Demethoxycarbonylation of methyl pheophorbide in DMF, water and NaCl gave methyl pyropheophorbide after refluxing for 60 min. The progress of reaction was monitored by HPLC. The baseline of HPLC chromatogram showed the presence of impurities (total, approx. 4%, by peak area). Addition of NaCl slightly increased the reaction rate, but also produced more impurities. A plot of percent methyl pyropheophorbide and methyl pheophorbide vs. reaction time is shown in FIG. 4.

C. Demethoxycarbonylation by benzene derivatives (100 mg) scale.

Demethoxycarbonylation of methyl pheophorbide was studied in sec-butyl benzene/water (4 equiv. & 16 equiv.), toluene/water (2 equiv.) and iodobenzene/water (16 equiv.). The reaction rates were much slower in this type of solvents compared to pyridine derivatives, and the reactions tended to give more impurities. The results are summarized in FIG. 21.

1. Toluene with water (2 equiv.)

Demethoxycarbonylation in toluene was first added 2 equivalents of water. The HPLC chromatogram showed <0.5% of methyl pyropheophorbide after 60 min. of reflux. With the intention of increasing reaction rate, additional water (16 equiv.) was added. After 110 min. of reflux (FIG. 5), HPLC of the reaction aliquot showed <1% of methyl pyropheophorbide indicating that the demethoxycarbonylation was not effective in this solvent. An impurity peak (approx. 1% peak area) very close to methyl pheophorbide was also observed, but not identified. The reaction was stopped after the 110 min draw.

2. sec-Butylbenzene a. With water (4 equiv.)

After refluxing for 110 min. in sec-butylbenzene/water (4 equiv.), 61% of methyl pyropheophorbide was observed (FIG. 6). Besides methyl pyropheophorbide, there were 4 major impurities observed by HPLC at levels between 1–4% b. With water (16 equiv.)

A similar reaction with 16 equivalents of water gave 48% of methyl pyropheophorbide after 90 min. of reflux (FIG. 7). An HPLC chromatogram of the 90 min pull showed significant amounts of impurities (total approx. 4% peak area). The reaction rate was slightly slower using 16 equiv. of water when compared to the reaction using 4 equiv. of water.

3. Iodobenzene with water (16 equiv.)

Demethoxycarbonylation reaction rate in iodobenzene/water (16 equiv.) was similar to that in sec-butylbenzene (16 equiv.), but had less impurity peaks. The HPLC of reaction aliquot after refluxing for 110 min. in iodobenzene/water showed 50% of methyl pyropheophorbide and 0.4% of total impurity peak area (FIG. 8).

D. Demethoxycarbonylation in 1-Nitropropane with water (16 equiv.)

The demethoxycarbonylation of methyl pheophorbide in 1-nitropropane/water was very slow compared to that in other solvents. The reaction showed only 8.7% of methyl pyropheophorbide after 30 min. of reflux (FIG. 9).

It will be apparent to those skilled in the art that various modifications and variations can be made in the method of the present invention without departing from the spirit or scope of the invention. Thus, it is intended that the present description cover the modifications and variations of this invention provided that they come within the scope of the appended claims and their equivalents.

What is claimed is:

1. A method for the demethoxycarbonylation of porphyrinic compounds, comprising:

reacting under sufficient conditions a porphyrinic compound of the formula I:

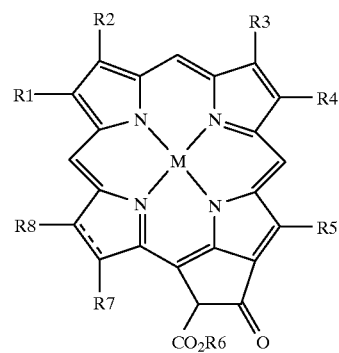

I with a high boiling point solvent to which water has been added in an amount ranging from about 1 to about 300 molar equivalents of water to the porphyrin starting material, for a time sufficient to produce a porphyrinic compound of the formula II:

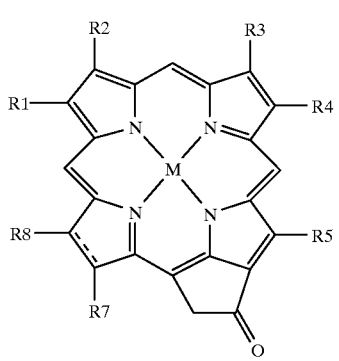

II wherein:

$R^1$–$R^8$ can be the same or different and are selected from: hydrogen, halide, alkyl, vinyl, functionalized alkyl, cyclic alkyl (1–6 carbons), substituted or unsubstituted aryl, substituted or unsubstituted alkenyl, substituted or unsubstituted alkynyl, amide, ester, CH=CHCH$_2$N(CH$_3$)$_2$, CH=CHCH$_2$N$^+$(CH$_3$)$_3$X$^-$ (where X is a charge balancing ion), CX$_2$CX$_3$ (where X is a halogen), NR$^9$R$^9$, CN, OH, OR$^9$, CHO, (CH$_2$)$_n$OH, (CH$_2$)$_n$SH, (CH$_2$)$_n$O-alkoxy, CH(OH)CH$_3$, CH(OR$^9$)CH$_3$, (CH$_2$)$_n$SR$^9$, (CH$_2$)$_n$OR$^9$ (where n=1, 2, 3, or 4, and R$^9$ is a functional group less than or equal to 100,000 daltons); $(CH_2)_nCO_{22}R^{10}$ (where $R^{10}$ is hydrogen, a physiologically acceptable salt, alkyl (1–6 carbons), substituted or unsubstituted aryl, substituted or unsubstituted alkenyl, or alkyne, and n=1, 2, 3, or 4); $(CH_2)_nCONHR^9$, $(CH_2)_nCON(R^9)_2$, $CO_2R^9$, $CONHR^9$, $CONR^9R^9$, $SR^9$ (where $R^9$ is a functional group less than or equal to 100,000 daltons); $SO_3R^9$, $SO_2NHR^9$, $SO_2N(R^9)_2$, $SO_2N(R^9)_2$, $SO_2N(R^9)_3{}^+X^-$ (where $R^9$ is a functional group less than or equal to 100,000 daltons and X is a charge balancing ion);

M can be $H_2$, Ag, Al, Ce, Co, Cr, Cu, Dy, Er, Fe, Ga, Hf, Ho, In, La, Lu, Mo, Mg, Nd, Pb, Pd, Pr, Pt, Rh, Sb, Sc, Sm, Tb, Th, Ti, Tm, U, V, Y, Tb, Zn, or Zr; and the bond between $R^7$ and $R^8$ is either a single bond or a double bond.

2. The method of claim 1, wherein water is added in an amount ranging from about 1 to about 200 molar equivalents of water to the porphyrin starting material.

3. The method of claim 1, wherein water is added in an amount ranging from about 1 to about 100 molar equivalents of water to the porphyrin starting material.

4. The method of claim 1, wherein water is added in an amount ranging from about 1 to about 50 molar equivalents of water to the porphyrin starting material.

5. The method of claim 1, wherein water is added in an amount ranging from about 1 to about 16 molar equivalents of water to the porphyrin starting material.

6. The method of claim 1, wherein the high boiling point solvent is selected from collidines, lutidines, picolines, pyridine, N,N-dimethylformamide, dimethylsulfoxide, xylenes, sec-butylbenzene, iodobenzene, and halogenated benzenes.

7. The method of claim 6, wherein the high boiling point solvent is 2,4,6-collidine.

8. The method of claim 6, wherein the high boiling point solvent is 2,3,5-collidine.

9. The method of claim 6, wherein the high boiling point solvent is 2,3,4-collidine.

10. The method of claim 6, wherein the high boiling point solvent is 2,4,5-collidine.

11. The method of claim 6, wherein the high boiling point solvent is 3,4,5-collidine.

12. The method of claim 6, wherein the high boiling point solvent is 2,3,6-collidine.

13. The method of claim 6, wherein the high boiling point solvent is 2,3-lutidine.

14. The method of claim 6, wherein the high boiling point solvent is 2,4lutidine.

15. The method of claim 6, wherein the high boiling point solvent is 2,5-lutidine.

16. The method of claim 6, wherein the high boiling point solvent is 3,4-lutidine.

17. The method of claim 6, wherein the high boiling point solvent is 3,5-lutidine.

18. The method of claim 6, wherein the high boiling point solvent is 2,6-lutidine.

19. The method of claim 6, wherein the high boiling point solvent is 3,6-lutidine.

20. The method of claim 6, wherein the high boiling point solvent is 2-picoline.

21. The method of claim 6, wherein the high boiling point solvent is 3-picoline.

22. The method of claim 6, wherein the high boiling point solvent is 4-picoline.

23. The method of claim 6, wherein the high boiling point solvent is pyridine.

24. A method for the demethoxycarbonylation of pheophorbides, comprising: reacting under sufficient conditions a pheophorbide compound of the formula III:

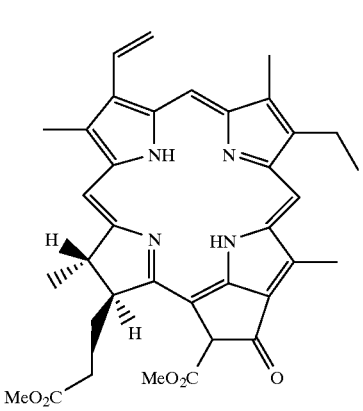

III with a high boiling point solvent to which water has been added in an amount ranging from about 1 to about 300 molar equivalents of water to methyl pheophorbide, for a time sufficient to produce a pyropheophorbide compound of the formula IV:

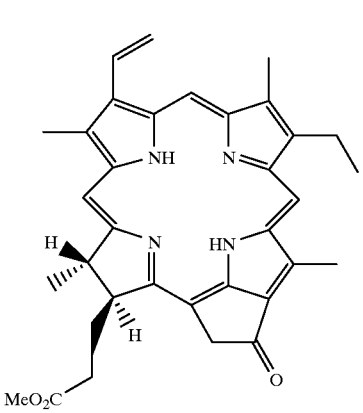

IV

25. The method of claim 24, wherein water is added in an amount ranging from about 1 to about 200 molar equivalents of water to the pheophorbide starting material.

26. The method of claim 24, wherein water is added in an amount ranging from about 1 to about 100 molar equivalents of water to the pheophorbide starting material.

27. The method of claim 24, wherein water is added in an amount ranging from about 1 to about 50 molar equivalents of water to the pheophorbide starting material.

28. The method of claim 24, wherein water is added in an amount ranging from about 1 to about 16 molar equivalents of water to the pheophorbide starting material.

29. The method of claim 24, wherein the high boiling point solvent is selected from collidines, lutidines, picolines, pyridine, N,N-dimethylformamide, dimethylsulfoxide, xylenes, sec-butylbenzene, iodobenzene, and halogenated benzenes.

30. The method of claim 29, wherein the high boiling point solvent is 2,4,6-collidine.

31. The method of claim 29, wherein the high boiling point solvent is 2,3,5-collidine.

32. The method of claim 29, wherein the high boiling point solvent is 2,3,4-collidine.

33. The method of claim 29, wherein the high boiling point solvent is 2,4,5-collidine.

34. The method of claim 29, wherein the high boiling point solvent is 3,4,5-collidine.

35. The method of claim 29, wherein the high boiling point solvent is 2,3,6-collidine.

36. The method of claim 29, wherein the high boiling point solvent is 2,3-lutidine.

37. The method of claim 29, wherein the high boiling point solvent is 2,4-lutidine.

38. The method of claim 29, wherein the high boiling point solvent is 2,5-lutidine.

39. The method of claim 29, wherein the high boiling point solvent is 3,4-lutidine.

40. The method of claim 29, wherein the high boiling point solvent is 3,5-lutidine.

41. The method of claim 29, wherein the high boiling point solvent is 2,6-lutidine.

42. The method of claim 29, wherein the high boiling point solvent is 3,6-lutidine.

43. The method of claim 29, wherein the high boiling point solvent is 2-picoline.

44. The method of claim 29, wherein the high boiling point solvent is 3-picoline.

45. The method of claim 29, wherein the high boiling point solvent is 4-picoline.

46. The method of claim 29, wherein the high boiling point solvent is pyridine.

* * * * *

UNITED STATES PATENT AND TRADEMARK OFFICE
CERTIFICATE OF CORRECTION

PATENT NO. : 5,973,141
DATED      : October 26, 1999
INVENTOR(S): Robinson et al.

It is certified that error appears in the above-identified patent and that said Letters Patent is hereby corrected as shown below:

IN THE CLAIMS

Claim 1, column 21, line 2, "$(CH_2)_n CO_{22} R^{10}$" should read --$(CH_2)_n CO_2 R^{10}$--.

Claim 14, column 21, line 49, "2,4lutidine" should read --2,4-lutidine--.

Signed and Sealed this

Sixth Day of June, 2000

*Attest:*

Q. TODD DICKINSON

*Attesting Officer*  *Director of Patents and Trademarks*